(12) United States Patent
Peyman et al.

(10) Patent No.: US 11,980,542 B2
(45) Date of Patent: *May 14, 2024

(54) OPTICAL IMPLANT AND METHODS OF IMPLANTATION

(71) Applicant: Gholam Peyman, Sun City, AZ (US)

(72) Inventors: Gholam Peyman, Sun City, AZ (US); Lisa Brothers Arbisser, Sarasota, FL (US)

(73) Assignee: Gholam Peyman, Sun City, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/118,071

(22) Filed: Mar. 6, 2023

(65) Prior Publication Data
US 2023/0200977 A1    Jun. 29, 2023

Related U.S. Application Data

(63) Continuation-in-part of application No. 17/697,726, filed on Mar. 17, 2022, now Pat. No. 11,596,513, which is a continuation-in-part of application No. 17/151,301, filed on Jan. 18, 2021, now abandoned, which is a continuation-in-part of application No. 16/827,106, filed on Mar. 23, 2020, now Pat. No. 10,925,723.

(51) Int. Cl.
*A61F 2/16* (2006.01)

(52) U.S. Cl.
CPC .... *A61F 2/1648* (2013.01); *A61F 2002/1681* (2013.01); *A61F 2002/16965* (2015.04)

(58) Field of Classification Search
None
See application file for complete search history.

(56) References Cited

U.S. PATENT DOCUMENTS

| | | | | |
|---|---|---|---|---|
| 4,437,194 A | * | 3/1984 | Hahs | A61F 2/16 623/6.51 |
| 4,463,458 A | * | 8/1984 | Seidner | A61F 9/007 623/6.43 |
| 4,596,578 A | * | 6/1986 | Kelman | A61F 2/16 623/6.17 |
| 4,790,845 A | * | 12/1988 | Grendahl | A61F 2/16 623/6.51 |
| 4,994,080 A | | 2/1991 | Shepard | |
| 5,245,367 A | * | 9/1993 | Miller | G02C 7/046 351/159.41 |
| 5,905,561 A | * | 5/1999 | Lee | B29D 11/00923 623/6.31 |

(Continued)

*Primary Examiner* — Leslie A Lopez
(74) *Attorney, Agent, or Firm* — The Law Office of Patrick F. O'Reilly III, LLC

(57) ABSTRACT

An apparatus has a central lens body for providing vision correction for a patient. The lens body has a central aperture and is configured as one of: a diffractive lens or a refractive lens. The lens body has at least one haptic extending from the lens body, and the central aperture has a form of a circular hole extending fully through the lens body when the apparatus is implanted in the eye. The lens body is formed from a substantially transparent material and the central aperture includes a darkened perimeter. The darkened perimeter of the central aperture includes a darkened internal wall extending through the lens body from an anterior surface to a posterior surface of the lens body.

17 Claims, 19 Drawing Sheets

(56) References Cited

U.S. PATENT DOCUMENTS

| | | | |
|---|---|---|---|
| 2005/0015143 A1* | 1/2005 | Willis | A61F 2/1608 |
| | | | 623/6.43 |
| 2008/0027537 A1* | 1/2008 | Gerlach | A61L 27/50 |
| | | | 623/6.22 |
| 2009/0021692 A1* | 1/2009 | Miller | G02C 7/042 |
| | | | 623/6.31 |
| 2009/0030513 A1 | 1/2009 | Valyunin | |
| 2011/0040376 A1* | 2/2011 | Christie | A61F 2/16 |
| | | | 623/6.43 |
| 2011/0295367 A1 | 12/2011 | Cuevas | |
| 2013/0053955 A1 | 2/2013 | Currie | |
| 2014/0277437 A1* | 9/2014 | Currie | A61F 2/1624 |
| | | | 623/6.37 |
| 2014/0379078 A1 | 12/2014 | Trindade | |
| 2016/0067035 A1 | 3/2016 | Gontijo | |
| 2016/0296662 A1* | 10/2016 | Stoy | A61L 27/52 |
| 2016/0374799 A1* | 12/2016 | McCafferty | A61F 2/1651 |
| | | | 623/6.34 |
| 2017/0273779 A1* | 9/2017 | Zhao | A61F 2/1654 |

* cited by examiner

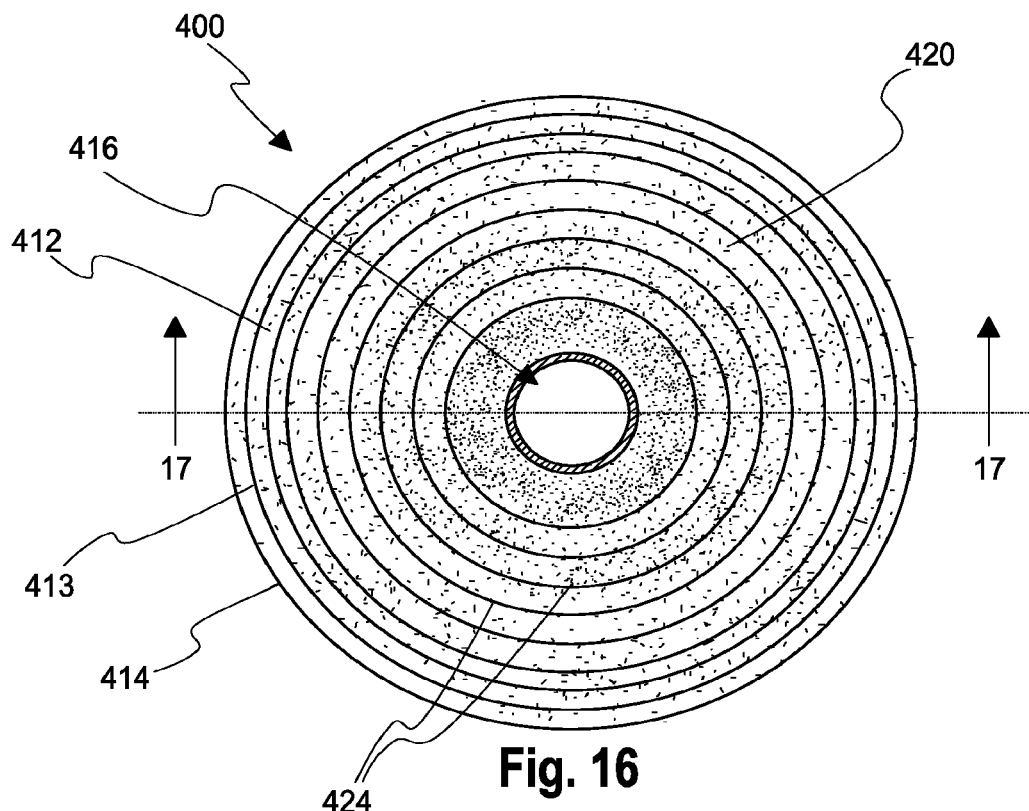
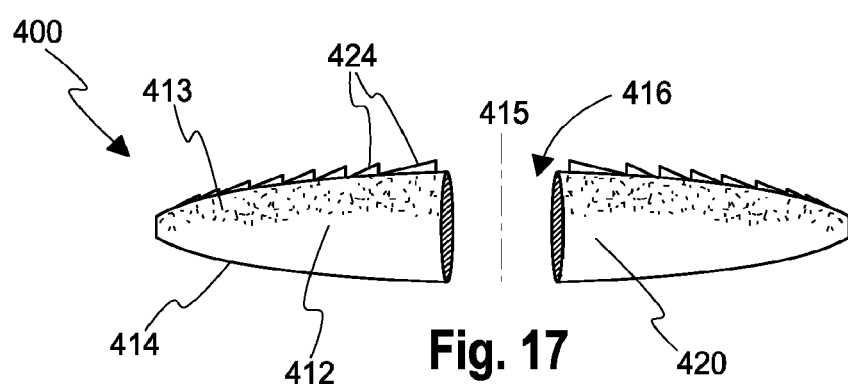

OPTICAL IMPLANT AND METHODS OF IMPLANTATION

CROSS-REFERENCE TO RELATED APPLICATIONS

This patent application is a continuation-in-part of U.S. patent application Ser. No. 17/697,726, entitled "Optical Implant And Methods Of Implantation", filed on Mar. 17, 2022, which is a continuation-in-part of U.S. patent application Ser. No. 17/151,301, entitled "Optical Implant And Methods Of Implantation", filed on Jan. 18, 2021, which is a continuation-in-part of U.S. patent application Ser. No. 16/827,106, entitled "Optical Implant And Methods Of Implantation", filed on Mar. 23, 2020, now U.S. Pat. No. 10,925,723, the disclosure of each of which is hereby incorporated by reference as if set forth in their entireties herein.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The present invention relates generally to the field of ophthalmic surgery, and more particularly, to an improved intraocular lens, lens mate apparatus, and improved methods for implanting an intraocular lens and lens mate apparatus into a human or animal eye.

2. Background

Cataract is one of the most common causes of blindness. Approximately 20.5 million (17.2%) Americans have a cataract in either eye, and these numbers are rising. Cataract is most commonly seen between the ages of 45-64, with a lower prevalence in males than in females. Its symptoms are manifested by progressive cloudiness of crystalline lens of the eye, leading to glare, myopic shifts, monocular diplopia, and gradual loss of vision. The comorbidities are environmental conditions such as UV exposure, altitude, occupation, diet, smoking, alcohol, medication such as steroids and diseases such as ocular inflammation (uveitis) diabetes mellitus and hypertension, as side effects of x-ray radiation and in children traumatic eye injuries and genetic predisposition. The cataract is classified depending on the stage of the lens opacification as incipient, immature, and mature and hypermature, or the location of lens opacities as cortical, nuclear, posterior subcapsular.

The treatment for cataract is surgical removal of the involved lens and is achieved by various methods. It is done under a regional anesthesia, topical anesthesia, retrobulbar anesthesia and peribulbar anesthesia, etc.

One method of treatment is intracapsular cataract extraction ("ICCE") in which the entire lens including the lens capsule is removed in one piece. This requires a relatively large 7-10 mm corneal incision through which the lens is expressed out of the eye. The procedure is seldom performed because of its numerous complications of corneal keratopathy, vitreous loss, wound leak, iris incarceration, high astigmatism, post-operative inflammation, cystoid macular edema, retinal detachment and high rate of the infection and corneal complications (bullous keratopathy). Following the operation, patients have been prescribed thick refractive glasses, which may be difficult to maintain on the patient's nose. The patients of this operation have been prone to falling when going down the stairs, and fractured bones were not an uncommon problem in these patients, even increasing the patient's mortality.

Another method of cataract treatment is extracapsular cataract extraction ("ECCE"), a procedure in which the lens cortex and nucleus is removed by an aspiration and irrigation system after removal of a part of the anterior capsule, while the rest of the capsule remains in place. This procedure has been performed most often in children having congenital cataract to avoid disrupting the posterior capsule to prevent vitreous loss. The surgery has been associated with serious post inflammatory response, glaucoma, proliferation of lens epithelial cells producing severe capsular opacification and fibrosis, and potentially retinal detachment when the posterior capsule has been inadvertently violated.

Yet another method of cataract treatment is extracapsular cataract extraction with phacoemulsification combined with intracapsular implantation of an acrylic intraocular lens ("IOL"). In this procedure, the lens cortex and nucleus are removed through a relatively small corneal incision, between about 4 mm to 5 mm in diameter, and an anterior capsulotomy. Then, an ultrasonically driven needle is used to emulsify the lens cortex and nucleus, which are then removed by an irrigation/aspiration of fluid and the lens cortical material. Subsequently, a folded IOL is implanted inside the lens capsule through a small corneal incision. While this concept has brought significant improvement to the technique of cataract surgery and benefit for the patient, the remaining lens epithelial cells have been found to attach to the anterior capsule, often proliferating posteriorly to produce a posterior capsular cloudiness and fibrosis which reduces post-operative visual acuity in the patient. Treatment of this complication involves either an yttrium aluminum garnet ("YAG") laser capsulotomy, or the removal of the part of the posterior capsule with a vitrectomy instrument by cutting and removing central part of the posterior capsule and the vitreous in order to clear the optical media. This procedure has been done routinely in the developed countries; however, it is not easily done in developing countries with a large cataract population because of the cost of a YAG-laser and/or the difficulty for the patient to return to a surgery center for an additional surgery.

An alternative procedure is to perform a limited central anterior and posterior capsulotomy in a single procedure, and the lens optic is implanted in the space of Berger located between the posterior lens capsule and anterior hyaloid membrane, while the lens haptics remain substantially in front of the lens capsule located in the posterior chamber contacting the ciliary body. When done properly, this procedure leaves a clear optical media in one surgical session without the need for subsequent need for the posterior capsulotomy. The lens capsule folds upon itself in this procedure.

In general, IOL implantation has a decades long history of biocompatibility in the eye. The IOLs are made from polymeric materials such as PMMA, silicone, hydrogel, polyvinylidene fluoride, or in combination with collagen as Collamer, multifocal IOLs are effective in providing near and far vision after cataract surgery. Toric IOLs are used to correct corneal astigmatism, such as the Alcon acrylic toric IOLs or the Johnson and Johnson Tecnis Toric 1-piece IOL.

Despite the advances in cataract surgery and the construction of the new IOLs, there are still some problems the patients have to deal with, that affect their visual satisfaction in the post-operative period.

For example, the IOLs can tilt either in a horizontal or vertical direction inducing great dissatisfaction for the patient. This happens frequently if the capsulotomy is not done properly or the lens zonulas are genetically affected in diseases such as in patients with Marfan syndrome, Morgagnian cataract, high myopia, or after traumatic injuries where the zonulas can become weak or broken, and the incomplete or partial lens zonulae contribute to a tilted IOL.

The IOLs can tilt or settle in the post-operative period as a result of capsular fibrosis after cataract surgery, for example, if the haptic and optics are inside the capsular bag and an uneven pressure is generated as a result of capsular fibrosis or a large capsulotomy.

IOLs seldom have a perfect refractive power to create an emmetropic refraction after surgery. In majority of cases the IOLs refractive power is off by plus or minus 0.5 D power or more, which is not easy to correct if the IOLs are multifocal lenses.

Lens centration is very important for multifocal lenses, otherwise patients are not satisfied with their vision and a lens exchange may be needed.

Children's eyes and myopic eyes grow significantly, requiring removal of the IOL and their replacement.

Capsular opacification occurs after the cataract surgery when the lens epithelial cells, located behind the anterior capsule, start proliferating inside the lens capsule to fill the empty space left inside the capsule after cataract extraction while the post-operative inflammatory response persists.

One prior art method for replacing the accommodative power of the crystalline lens has been to implant a prior art multifocal IOL. However, such lenses have had shortcomings in that if they were not perfectly corrected for far vision, the rest of the prior art multifocal IOL zones would not be perfectly corrected either. Further, the prior art multifocal IOL has been prone to de-centration issue or double vision.

A need remains for a patient to have only a single operation to correct the patient's vision over the lifetime of the patient, even for patients that are infants or minors.

In standard intraocular lenses, the light refracts depending on the surface curvature of the lens and its index of refraction and the adjacent media. The surface of the refractive lens is very smooth to prevent light scattering. Light travels through diffractive lenses differently than through the standard refractive lenses. The surface of the standard IOL can be converted to a diffractive lens. In this case the IOL works like a composite of small prisms and the surface of the lens is visibly separated by prismatic height and valleys that divert the light toward the desired direction to create a focal point from an object located in front of the eye at different distances such as near, intermediate distance, or far. However, unwanted visual effects can be caused by the superposition of unfocused and focused images, creating halos or starbursts from the incoming light, such as traffic light, etc.

In general, bifocal, or multifocal, lenses are desirable for providing in focus intermediate distance, e.g., for reading, etc. In diffractive lenses, the prismatic up and down steps created on the surface of the IOL can be homogenous but the distance between each micro prism becomes smaller from the lens center (near the optical axis) to the peripheral portion of the lens. These micro-prisms convert the monofocal IOL to a bifocal or trifocal or multifocal IOL, so that the focal point of the lens is collected on a distinct distance from the IOL surface while the intermediate distances remain not focused continuously.

Diffractive lenses can be also constructed where the step height of certain zones are intermittently variable compared to the adjacent zones. However, this configuration is also similar to all diffractive lenses of the prior art in that it will not eliminate the minor incoming light scattering which appears as halos at night from the approaching traffic. The central zone of such an IOL acts as a refractive lens for focusing the images on the central retina with specific fixed dioptric power for each eye such as myopia or hyperopia. The refractive power of the central area in all diffractive lenses are predetermined prior to the implantation and, as such, they can vary by a predetermined dioptric power between a minus to plus that is fixed.

Congenital cataract is referred to as opacities of crystalline lens which are present at birth. Congenital cataract might be unilateral or bilateral. In general, the lens opacities are caused by genetic predisposition or most likely after infection of the pregnant mother with various viruses, taking certain medication, having diabetes, or trauma or inflammation during the pregnancy.

Genetically induced congenital cataract (CC) can be an autosomal dominant, autosomal recessive, or X-linked such as galactosemia, diabetes, Wilson's disease, trisomy 21, which can be diagnosed by genetic evaluation of the child and parents. Congenital cataract also can be associated with other ocular abnormalities such as aniridia, iris coloboma, in zonular dehiscence, microcornea or megalocornea.

The lens opacities can involve the front part of the lens (anterior polar cataract), the posterior part of the lens (posterior polar cataract), or the central part of the lens (nuclear cataract), or it may be caused by persistent fetal vasculature (PFV).

The incidence of congenital cataract is 5-20% of the childhood cataract or 3.18 cases per 10,000. The rest are caused by trauma/abuse, accounting for 49% of the cataracts in children. Infectious disease of the mother during the pregnancy that causes cataract include syphilis, rubella, toxoplasmosis, varicella, herpes simplex, herpes zoster, Epstein-Barr virus, influenza, poliomyelitis, or a medication taken during the pregnancy, such as a tetracycline medication.

Laboratory work up includes titers for syphilis in a form of a venereal disease research laboratory test (VDRL), other viruses, toxoplasma, herpes simplex, zoster, Epstein-Barr virus (EBV), serum calcium and phosphorus levels and urine for reducing certain substances.

The symptoms of congenital cataract are white appearing pupil, loss of red reflex, strabismus, amblyopia ("lazy eye"), nystagmus and lack of fixation and in the future leading to reading disability. Because of the urgency of making a diagnosis, the children should be examined soon after birth, but no later than 6 months of age.

Evaluation of the eye should include slit lamp examination of the cornea, lens, intraocular pressure (TOP) measurement, and ultrasound examination of the fundus when the view is obstructed. The differential diagnoses of congenital cataract are retinoblastoma, persistent fetal vasculature (PFV), colobomas, Coats disease, vitreous hemorrhage, and toxocariasis, etc.

There are several surgical procedures for treatment of congenital cataract. Except for the lens opacity of less than 3 mm, the lens should to be removed and the refractive power of the eye needs to be corrected to prevent amblyopia. If the lens opacity is less than 3 mm and the child can fixate, the surgery may be delayed for the eye to grow larger. However, if the child is fixating with one eye only, the amblyopia may force the surgeon to remove the cataract. The children will need to be evaluated for their ability to fixate and follow the light or one can induce optokinetic nystagmus to see the eye's movement or evaluate the retinal function with visual evoked potential or evaluation of the eye for presence of strabismus, IOP, corneal diameter, and evaluation of the retina, including the use of ultrasound.

Despite the advances in cataract surgery and the construction of the new IOLs, there are still some problems the patients have to deal with, that affect their visual satisfaction in the post-operative period, which the present invention seeks to address.

BRIEF SUMMARY OF THE INVENTION

The inventors of the present invention have discovered an improved intraocular lens construction for implantation into an eye and novel methods for implanting the improved intraocular lens within the eye.

According to one form of the present invention, an apparatus or lens for implantation in the eye. The lens includes a body shaped and sized for providing vision correction for a patient. The lens body has a central aperture and is configured as one of a diffractive lens or a refractive lens.

In one form of the present invention, the lens body is formed from a substantially transparent material and the central aperture includes a darkened perimeter. In one preferred form, the darkened perimeter of the central aperture includes a darkened internal wall extending through the lens body from an anterior surface to a posterior surface of the lens body.

In another form of the present invention, the lens body has a first index of refraction and is formed from at least one material configured to have a second index of refraction when subjected to a laser and/or radiation.

According to another form of the present invention, the central aperture includes a plug or insert received within the central aperture. In a preferred form, the interface between the insert and the lens body defines a darkened perimeter of the central aperture. In another preferred form, the insert has the form of a cone, a cylinder, or a spring received within the central aperture.

In one form of the present invention, the lens body includes a UV-absorbent peripheral portion.

According to another form of the present invention, central aperture has the form of a circular hole extending fully through the thickness of the lens body and is preferably centered on an optical axis of the lens.

In still another form of the present invention, the lens includes one or more stabilizing haptics extending from the lens body.

In one form of the present invention, the central aperture has the form of an annular mask located on one of an anterior surface or a posterior surface of the lens body.

According to one aspect of the present invention, the lens is provided in combination with another intraocular lens in the eye, and the lens is arranged such that it overlies and is anterior of the other intraocular lens when implanted in the eye.

According to yet another aspect of the present invention, the lens body includes an anterior surface having a sprayed coating of a nanoparticle composition to produce a nanostructured surface.

In another form of the present invention, the lens further includes: a first femtosecond laser modified index of refraction zone proximate to, and surrounding, the central aperture; and a second femtosecond laser modified index of refraction zone located at a peripheral portion of said lens, surrounding the central aperture, for providing an expanded panoramic image to the peripheral retina of a user of the lens.

According to yet another aspect of the present invention, the lens includes: a first femtosecond laser modified index of refraction zone covering about 20% of the total surface area of an anterior surface of the lens body, the first zone being configured for near focus; a second femtosecond laser modified index of refraction zone covering about 40% of the total surface area of the anterior surface of the lens body being configured for intermediate focus; and a third femtosecond laser modified index of refraction zone covering about 40% of the total surface area of the anterior surface of the lens body being configured for far focus.

According to one form of the present invention, a method of implanting the lens in an eye includes the steps of obtaining and implanting the lens in the eye and applying a femtosecond laser to the lens body to change its initial index of refraction in situ.

According to yet another aspect of the present invention, the lens is in a form of a collamer lens configured to be implanted in front of an existing natural lens of the eye or an existing intraocular lens, and behind the iris of the eye.

Other features and advantages of the present invention will become readily apparent from the following detailed description, the accompanying drawings, and the appended claims.

BRIEF DESCRIPTION OF THE SEVERAL VIEWS OF THE DRAWINGS

The invention will now be described, by way of example, with reference to the accompanying drawings, in which:

FIG. 5 shows the central lens body tucked behind the anterior and posterior capsule and the lens haptics located overtop of the anterior and posterior capsule;

FIG. 6 shows the central lens body tucked behind the anterior and posterior capsule and the lens haptics located overtop of the anterior and posterior capsule;

FIG. 7 shows the central lens body located overtop of the anterior and posterior capsule and the lens haptics tucked behind the anterior and posterior capsule;

FIG. 8 illustrates the location of the lens body relative to the lens capsule in the first configuration of FIG. 6 (solid line) and further illustrates the location of the lens body relative to the lens capsule in the alternative configuration of FIG. 7 (phantom line);

FIG. 12 shows the lens mate mechanically engaging the haptics of the intraocular lens;

FIG. 16 illustrates a top plan view of another embodiment of a diffractive lens or a lens mate according to the present invention, and FIG. 16 omits the haptics of the lens for illustrative purposes;

FIG. 17 illustrates a cross-sectional view of the lens of FIG. 16 taken along view line 17-17 in FIG. 16;

FIG. 19 illustrates the mask located on the anterior surface of the lens body;

FIG. 20 illustrates an alternative configuration of the lens wherein the mask is located on the posterior surface of the lens body;

FIG. 22 illustrates the plug members prior to assembly with the lens of FIG. 21;

FIG. 23 illustrates the plug member in the form of a cylindrical spring assembled within the aperture of the lens body;

FIG. 24 illustrates the plug member in the form of a conical spring assembled within the aperture of the lens body;

FIG. 25 illustrates the plug member in the form of a U-shaped, hollow plug assembled within the aperture of the lens body;

FIG. 29 illustrates an alternative configuration whereby the haptics are cut or released;

FIG. 42 shows the central lens body tucked behind the anterior and posterior capsule and the lens haptics located overtop of the anterior and posterior capsule;

FIG. 43 shows the central lens body located overtop of the anterior and posterior capsule and the lens haptics tucked behind the anterior and posterior capsule;

Throughout the figures, the same elements are always denoted using the same reference characters so that, as a general rule, they will only be described once.

DETAILED DESCRIPTION OF EMBODIMENTS OF THE INVENTION

Figure 1:
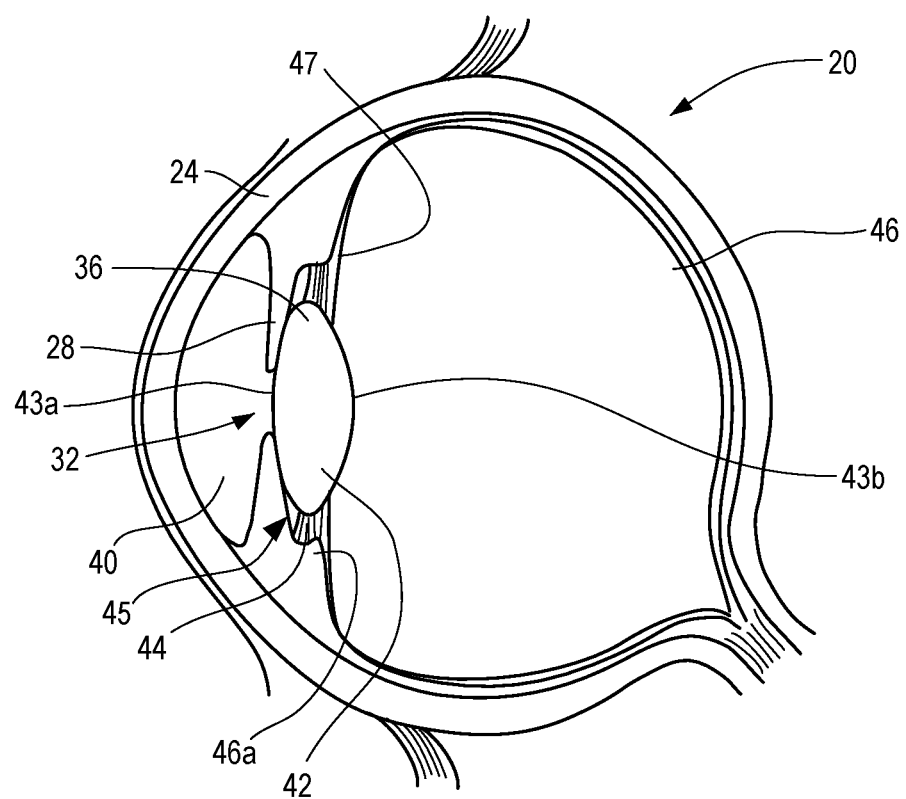
FIG. 1 is an enlarged, diagrammatic view of a human eye.

While the present invention is susceptible of embodiment in various forms, there is shown in the drawings and will hereinafter be described a presently preferred embodiment of the invention, with the understanding that the present disclosure is to be considered an exemplification of the invention, and is not intended to limit the invention to the specific embodiment illustrated.

Figure 2:
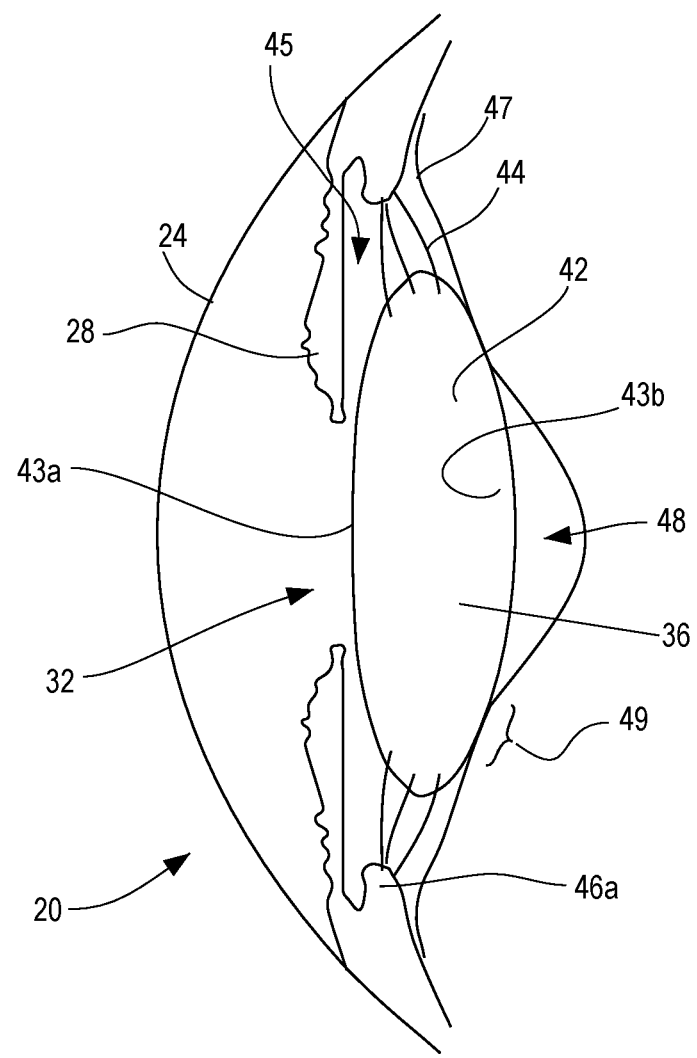
FIG. 2 is a greatly enlarged, diagrammatic view of the anterior segment of the human eye.

FIGS. 1 and 2 show a diagrammatic view of the human eye 20. Beginning at the exterior of the eye 20, the eye 20 has a protective outer layer or cornea 24 which retains the fluids or aqueous humor of the eye 20 and which focuses light. Inward of the cornea 24 is the ring-like iris 28 with an aperture or pupil 32 for restricting light reaching the lens 36. The lens 36 defines the posterior extent of the anterior segment 40 of the eye 20, sitting behind the iris 28. The lens 36 is composed of protein encased in a capsular bag 42. Supporting ligaments or zonules 44, composed of 360 degrees of attachments anterior, equatorial, and posterior, and together with Weigert's ligament (49 in FIG. 2) which defines the space of Berger (48 in FIG. 2), stabilize, and center the capsular bag 42 within the eye 20. Opposing the anterior segment 40 of the eye 20 is the posterior segment 46 containing the vitreous body, optic nerves, veins, and arteries of the eye 20. The capsular bag 42 has a forward or anterior wall or portion 43a and a rearward or posterior wall or portion 44b that together retain the denser, hard lens nucleus and the surrounding, less dense lens cortex. A crevice or sulcus 45 exists between the iris 28 and the ciliary body 46a. The anterior hyaloid membrane 47 is located behind the capsular bag 42 and separates the vitreous humor of the eye from the anterior segment 40.

Figure 6:
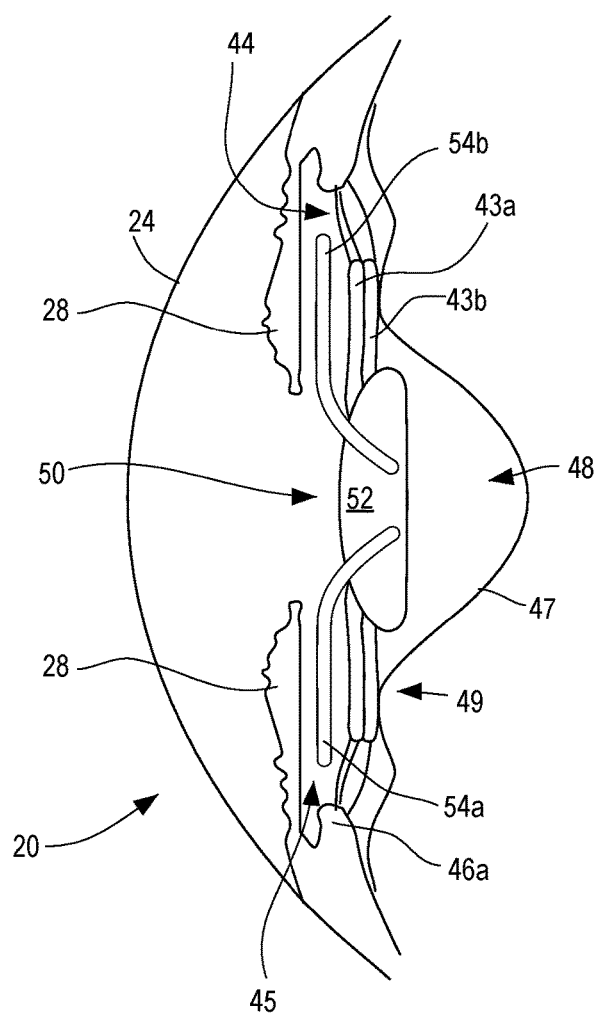
FIG. 6 is an enlarged, side elevation diagrammatic view of the intraocular lens shown in FIG. 3 implanted within the human eye.
Figure 7:
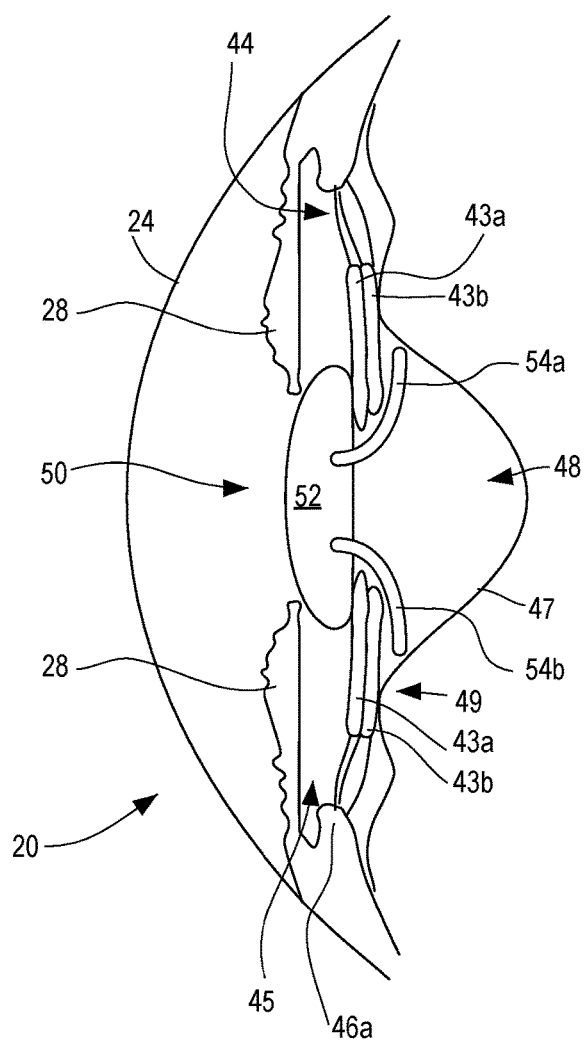
FIG. 7 is an enlarged, side elevation diagrammatic view of the intraocular lens shown in FIG. 3 implanted in an alternative configuration within the human eye.
Figure 8:
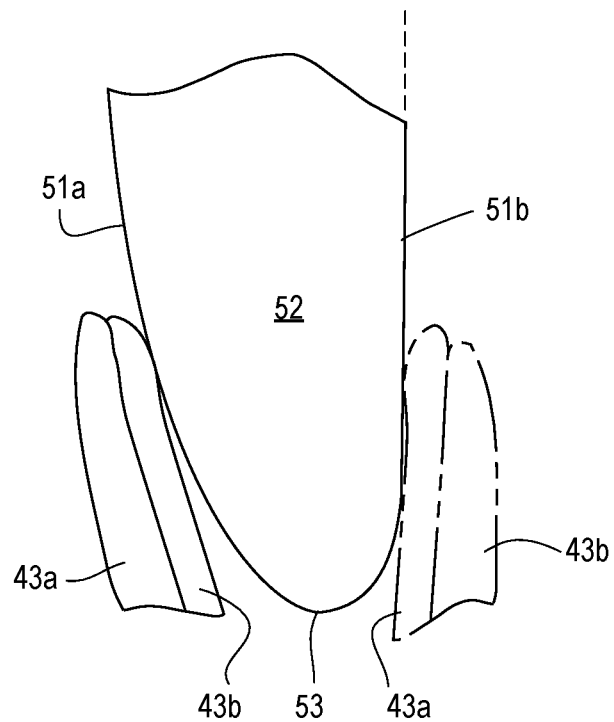
FIG. 8 is a greatly enlarged, detailed side elevation diagrammatic view of the engagement of the intraocular lens shown in FIG. 3 with the lens capsule.

As will be discussed in greater detail hereinafter, the inventors have developed advantageous methods for the prevention or minimization of the likelihood of proliferation of lens epithelial cells after the ECCE procedure discussed above. In one preferred method, a bio-compatible adhesive, such as FDA-approved synthetic polyethylene glycol hydrogel sealant sold under the trade name ReSure Sealant by Ocular Therapeutix, Inc. of Bedford Mass., is injected into the capsule after ECCE to seal the emptied anterior capsular portion 43a and posterior capsular portion 43b tight (hereinafter, the sealed portions 43a and 43b, which are illustrated in FIGS. 6-8, may collectively be referred to as "leaflets"), so that substantially no free space remains within the capsular bag 42 where aqueous and inflammatory cytokines may ingress and stimulate cell proliferation. The injection of bio-adhesives along with an anti-inflammatory agent, such as dexamethasone at low concentration of about 100 micrograms-400 micrograms per 0.05 milliliter ml or more, or in combination with an antibiotic may be done using a small 27 gauge needle either before or after IOL implantation to slowly release the medication and prevent separation of the capsular bag leaflets after the surgery and to prevent inflammation and/or infection and the growth of the anterior lens epithelial cells inside the capsule.

The bio-compatible tissue adhesive that is injected inside the leaflets 43a and 43b may require ultraviolet radiation to permanently close or seal the space between the leaflets 43a and 43b to prevent lens epithelial cell proliferation and capsular opacification. The tissue adhesive can be made to of absorbable or non-absorbable polymers. Preferably, the biocompatible adhesive does not induce any refractive change of the IOL that is implanted subsequent to the sealing of the leaflets 43a and 43b, and the adhesive is spaced or separated completely from the IOL.

The inventors believe that sealed lens capsule leaflet (43a and 43b) may hold an IOL tight to provide a better forward and backward motion of the lens capsule and IOL, as compared to the prior art ECCE implantation methods, during the accommodation or contraction of the ciliary body muscles for seeing near objects or far objects as would happen with the normal, healthy eye.

FIGS. 3-8 show one preferred, improved intraocular lens (IOL) 50 embodying the principles of the present invention. Attendant to a phacoemulsification procedure for removal of the natural lens nucleus and cortex from the capsular bag 42, the IOL 50 is especially suited for the implantation techniques that will be discussed in detail hereinafter. The lens 50 has a central lens body or optic 52 made from a biocompatible transparent polymeric material such as PMMA, silicone, hydrogel, or acrylic, and portions of which may be hydrophobic, hydrophilic, or amphiphilic, or a combination thereof.

With reference now to FIG. 8, the central lens body 52 has a first and second, opposite anterior (anterior with respect to the frontal plane) and posterior (posterior with respect to the frontal plane) surfaces 51a and 51b, respectively. The posterior surface 51b of the lens body 52 generally resides in a plane 55. The central lens body 52 has a suitable cross-sectional configuration for providing vision correction for the patient, which is known in the art. The anterior surface 51a and posterior surface 51b of the central lens body 52 meet or join in a rounded peripheral or side surface 53. As will be discussed in detail hereinafter, one or more of the surfaces of the lens body 52 are especially suited for engaging the sealed leaflets 43a and 43b of the capsular bag 42. To this end, one or more of the surfaces 51a, 51b, and/or 53 may be treated with a surface treatment or applied layer of a different material, or made from a material that is different from the remaining portion of the lens body 52, to enhance sealing of the lens body 52 with the sealed leaflets 43a and 43b.

The lens body 52 may have one or more surfaces of a varying degree of convexity depending on the need for correction to the patient's vision. The lens body 52 may have a toric or spherical shape, a positive dioptric power, or possess multiple focal points to correct a patient's vision as is known in the art.

Figure 3:
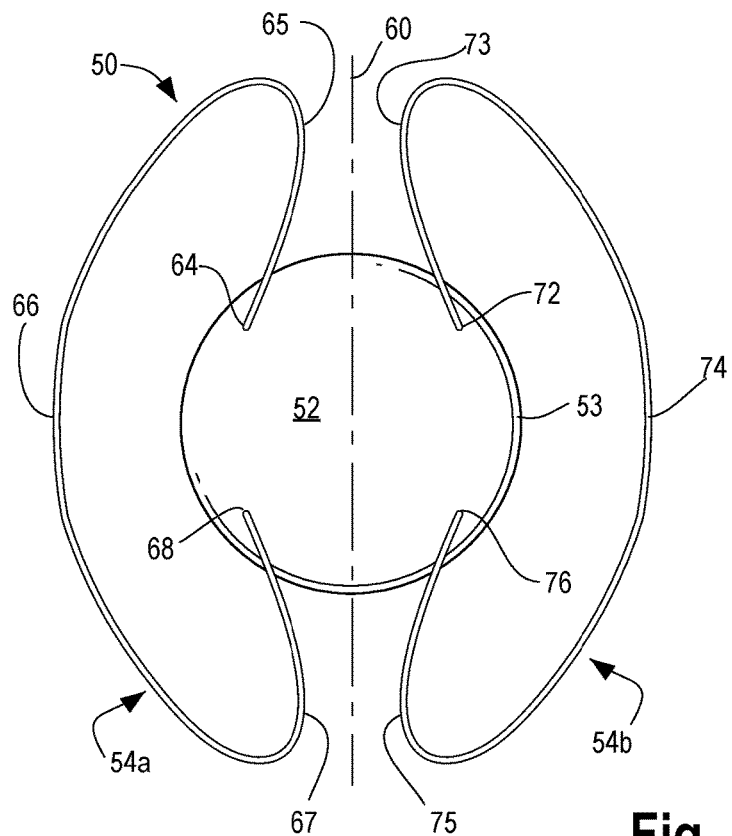
FIG. 3 is an enlarged, top plan view of an embodiment of an improved intraocular lens according to the present invention.

Referring to FIG. 3, the lens 50 further preferably includes a pair of haptics 54a and 54b extending from the central lens body 52 in a bi-lobular or "butterfly" configuration that surrounds the circular optic in a semi-oval fashion creating two wings that connect the superior portion of the lens body 52 to its inferior part. The haptics 53a and 54b are inserted or connected to the lens body 52 in either (i) a parallel fashion with respect to the plane of the posterior surface 51b of the lens body 52, or (ii) an angled or offset fashion with respect to the plane 55 defined by the posterior surface 51b of the lens body 52, producing a slight separation or angle between the plane 55 of the posterior surface 51b of the lens body 52 and attachment points of the haptics 54a and 54b, whereby the leaflets 43a and 43b of the lens capsule 42 may sit comfortably against the lens 50 and contribute to the closure of the space between the anterior and the posterior capsule (FIG. 6 or 7) to prevent or at least minimize the likelihood of capsular opacification, tilt and provide balance and stability to the IOL 50 within the eye.

With reference to FIG. 3, the haptics 546a and 54b are generally symmetric about a central axis 60 of the IOL 50. The path of the haptic 54a, which is generally kidney shaped, includes a first point of connection 64 to the lens body 52 and extends toward the central axis 60 before curving back away from the central axis 60 at a first distal end 65. From the first distal end 65, the haptic 54a extends away from the central axis 60 in an arc toward a medial point 66, at which point the haptic 54a curves back toward the central axis 60. The haptic 54a includes a second distal end 67 where the haptic 54a curves back away from the central axis 60 to a second point of connection 68.

Still referring to FIG. 3, the path of the haptic 54b includes a first point of connection 72 to the lens body 52 and extends toward the central axis 60 before curving back away from the central axis 60 at a first distal end 73. From the first distal end 73, the haptic 54b extends away from the central axis 60 in an arc toward a medial point 74, at which point the haptic 54b curves back toward the central axis 60. The haptic 54b includes a second distal end 75 where the haptic 54b curves back away from the central axis 60 to a second point of connection 76.

As will be discussed below, the haptics 54a and 54b have a configuration that may be advantageously engageable with the ciliary body 46a for stabilizing the lens 50 (FIG. 6). Alternatively, the haptics 54a and 54b may be located behind the leaflets 43a and 43b for stabilizing the lens 50 (FIG. 7).

Figure 4:
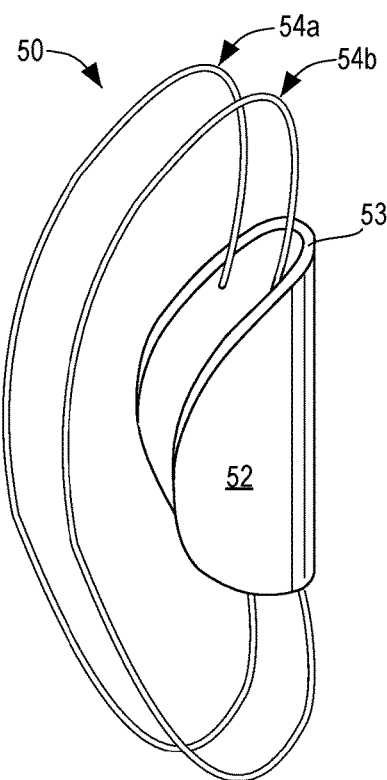
FIG. 4 is an enlarged, perspective view of the intraocular lens shown in FIG. 3 in a folded configuration prior to being implanted within the human eye.
Figure 5:
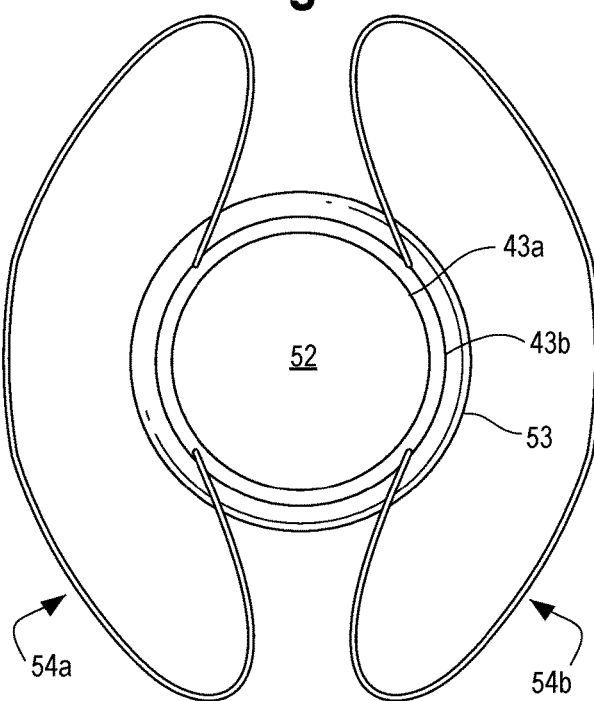
FIG. 5 is an enlarged, top plan diagrammatic view of the intraocular lens shown in FIG. 3 implanted within the human eye.

With reference to FIG. 4, the lens 50 would be implanted using standard or customized injectable technology by folding it and injecting it in the desired location within the eye along with a viscoelastic material through a very small incision in the cornea 24. The viscoelastics would then be washed away with saline solution after implantation to prevent rise in the intraocular pressure.

With reference now to FIG. 6, in one preferred configuration of implantation of the IOL 50, the lens body 52 or optic is positioned in the space of Berger 48, such that the leaflets 43a and 43b lie overtop of the lens body 52. In this configuration, the haptics 54a and 54b lie substantially (e.g., almost entirely) over the anterior capsule 43a, and may lie on the zonulas 44 (if intact), or may reach the ciliary body 46a to make the IOL 50 independent from the lens capsule 42 in case the weak or ruptured zonulas 44. The haptics 54a and 54b may reach or touch the sulcus 45 between the ciliary body 46a and the iris 28 (not illustrated). Contact between the haptics 54a and 54b with the ciliary body 46a is also limited to two points on each side of the lens body 52 to limit the undesirable uncontrolled penetration of the lens haptic 54a and 54b inside the ciliary body 46a, which could cause bleeding or irritation or inflammation in the eye. The inventors believe that the configuration of the bi-lobe haptics 54a and 54b may provide a better-balanced lens optic or lens body 52 and create a better centration for the lens body 52 to prevent or minimize the likelihood of tilting of the IOL 50.

With reference now to FIG. 7, in one alternative configuration of implantation of the IOL 50, the lens body 52 or optic is positioned behind the iris 28 such that it lies overtop of the leaflets 43a and 43b to balance the lens optic or lens body 52 and create a better centration for the lens body 52 to prevent or minimize the likelihood of tilting of the IOL 50.

The inventors believe that in the IOL 50 implantation configuration illustrated in FIGS. 5, 6, 7, and 8, the lens body 52 or optic acts like a plug to close the opening in the posterior or anterior chamber preventing penetration of the vitreous into the anterior chamber, which would have undesirable complications.

In an alternative configuration, not illustrated, the IOL 50 is implanted such that lens body 52 is located in an intermediate position, within the lens capsule 42.

The inventors of the present invention believe that the IOL 50 and the methods of implantation described above may be beneficial to prevent or at least minimize the likelihood of secondary cataract of the posterior portion 43b of the lens capsule 42 such that duplicative or remedial surgeries, common with prior art surgical procedures and lens designs, may be minimized or eliminated over the lifetime of the patient.

In another embodiment, the IOL 50 can act as an additional, or secondary IOL to a normal crystalline lens to correct either a high myopic eye.

In another embodiment, the IOL 50 can be positioned over an existing IOL in a previously operated upon eye to compensate for the existing refractive errors of the eye eliminating the need for a complex surgery of removing an existing IOL from its capsular bag and eliminating or reducing post-operative trauma contributing to a faster visual rehabilitation and wound healing.

Figure 9:
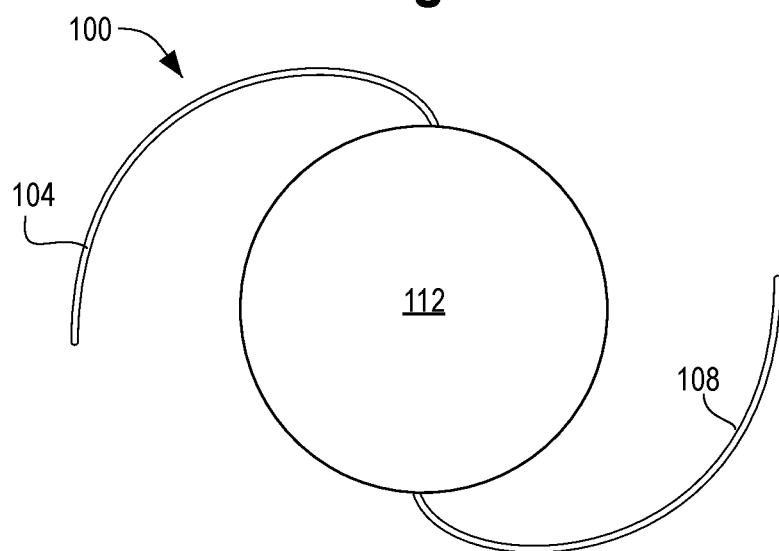
FIG. 9 illustrates a top plan view of a secondary intraocular lens that may be implanted overtop of the intraocular lens shown in FIG. 3.

In one embodiment, the surgical methods disclosed herein may be modified for younger patients, adults, or children, in whom the eye grows and requires a different refractive correction over time. In such a modified method, a secondary IOL such as the IOL 100 illustrated in FIG. 9 is implanted over, e.g., in front of, the initially implanted intraocular lens 50. The secondary IOL 100 includes a pair of haptics 104 and 108 which have discrete endpoints or poles, and which are not in the form of loops. The secondary IOL 100 further includes an optic or lens body 112, which may be a plus, a minus or a toric IOL depending on the patient's need. The secondary IOL 100 is preferably implanted with its haptics 104 and 108 positioned generally 90 degrees relative to the haptics 54a and 54b of the inventive IOL 50 (e.g., generally extending perpendicular to the central axis 60) such that the haptics 104 and 108 are located over the existing crystalline lens or zonulae 44 in the posterior chamber behind the iris 28. The secondary IOL 100 and the IOL 50 are separated or spaced from each other at all times.

The secondary IOL 100 is generally self-maintained in the eye due to the structure of its haptics 104 and 108 and the structure of the eye, and the secondary IOL 100 does not adhere to the lens capsule 42. Thus, the secondary IOL 100 can be easily removed or replaced without tearing or cutting the tissue of the eye.

The stacked positions of these two IOLS 50 and 100 might have an implication in creating an accommodative lens where the lenses get closer to each other and separate from each other depending on the accommodative process and contraction of the ciliary muscles and their pull on the lens, zonulas/capsule pulling it forward or relaxing it backward.

In another embodiment of the present invention, one can modify the index of refraction of the IOL 50 or 100 non-invasively by changing its index of refraction using a femtosecond laser as needed throughout the patient's life. In some applications, the IOL 50 or 100 has a fixed refractive power. However, the refractive index of the IOL 50 or 100 can be modified to create bifocal, trifocal, multifocal or toric lens prior to the surgery or afterward using nanojoule pulses of a femtosecond laser applied to the surface of the IOL 50 or 100. The IOL 50 or 100 may be provided with an extra soft polymeric surface such as crosslinked collagen. The inventors believe that such a lens would prevent or at least minimize the likelihood of the problems associated with multi focal lenses which include, tilt, capsular opacification, off-axis positioning, and the difficulty of lens exchange.

In one form, the surface of the IOL 50 or 100 is exposed to low energy nanojoule femtosecond pulses to modify the index or the refraction of the lens 112 to the desired power and the control of a wave front technology unit to accurately provide accurate femtosecond pulses to the lens surface and create an emmetropic refraction or multifocal refraction as desired for the patents' need.

Figure 10:
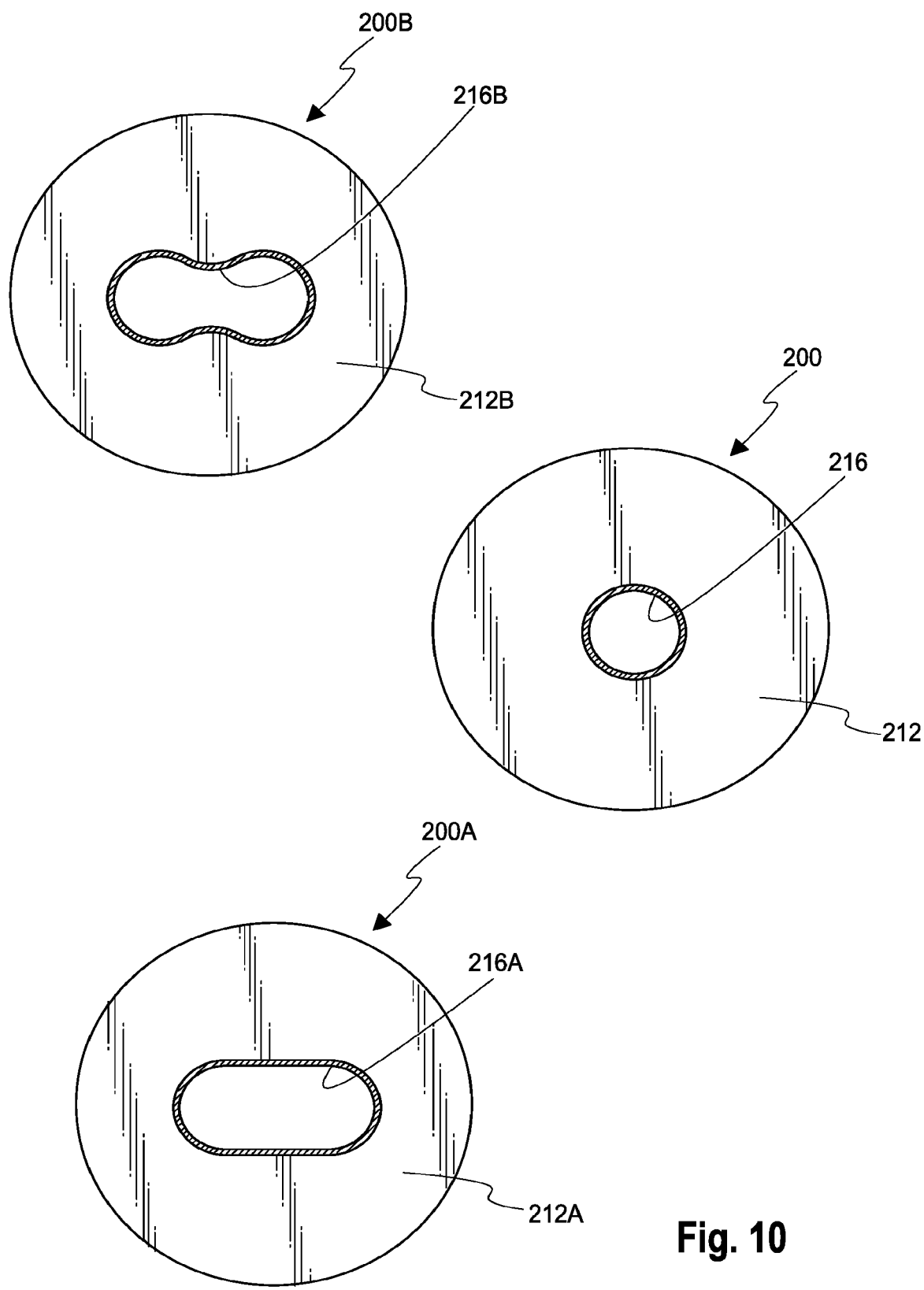
FIG. 10 illustrates a top plan view of three different embodiments of a lens mate or secondary body that may be implanted overtop (anterior) of an intraocular lens, such as that shown in FIG. 3, whereby the refractive power of the lens mate may be modified in situ using a laser.

Referring now to FIG. 10 a secondary body may be provided in the form lens mate 200, which is a substantially flat plate or disc, oval, or thin cylinder, for being implanted over, i.e., in front of, or anterior to, an implanted intraocular lens, such as the aforementioned lens 50 or a commercially available prior art IOL. The first illustrated embodiment of the lens mate 200 includes an optic or lens body 212 that is free of any haptics, and which preferably has no correction (i.e., is optically neutral) at the time that the lens mate 200 is implanted in the eye. The body 212 is preferably between 4.0-8.0 mm in diameter with a thickness (out of the plane of view in FIG. 10) of between about 0.05 mm and 3.0 mm. The lens body 212 includes a central hole or aperture 216 that may be between about 1.0 and about 3.0 mm in diameter. The aperture 216 is surrounded by a darkened portion of the lens body 212 or wall along its perimeter to prevent or minimize light scattering, and rendering a pin hole effect to the light by extending the focal point area for the near objects and focusing on the distant objects for a patient.

Figure 13:
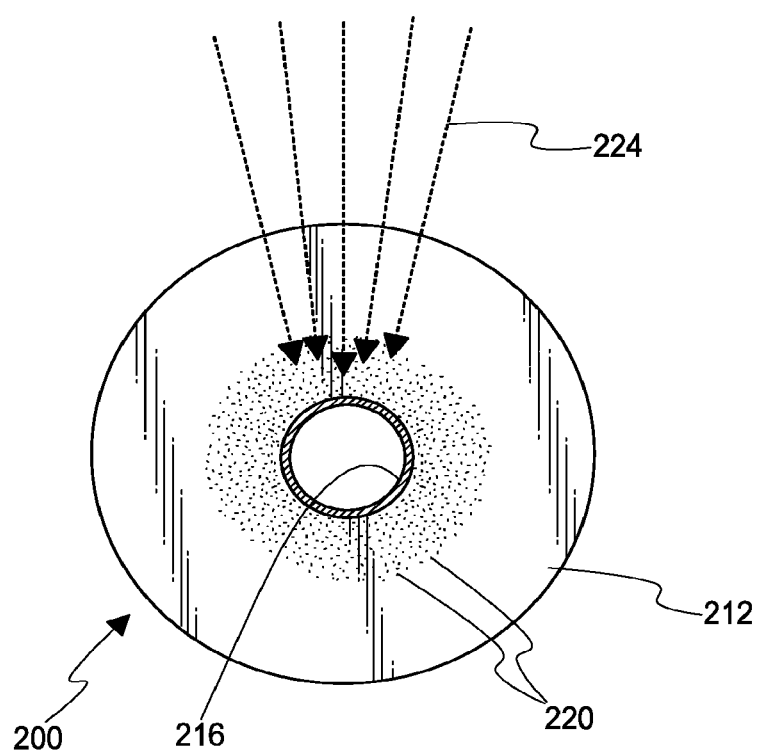
FIG. 13 illustrates a diagrammatic top plan view of one of the three different embodiments of the lens mate shown in FIG. 10 being subjected to a femtosecond laser to modify its refractive power in a zone around a central aperture subsequent to implantation in the eye.

The lens mate 200 is preferably formed from one or more semi-flexible, flexible, or foldable transparent polymeric materials such as PMMA, acrylic, silicone, hydrogel, or combination of silicone hydrogel or crosslinked collagen or elastin, etc. such that the body 212 index of refraction may be modified non-invasively by using a femtosecond laser as needed throughout the patient's life. In some applications, the lens mate 200 has a fixed refractive power. However, the refractive index of the lens mate 200 preferably can be modified to create bifocal, trifocal, multifocal or toric lens prior to the surgery or afterward using nanojoule pulses of a femtosecond laser applied to the surface of the body 212 as will be discussed in greater detail below. The body 212 may be provided with an extra soft polymeric surface such as crosslinked collagen. The inventors believe that such a lens mate 200 would prevent or at least minimize the likelihood of the problems associated with multi focal lenses which include, tilt, capsular opacification, off-axis positioning, and the difficulty of lens exchange. The refractive power of the lens body 212 is corrected as needed, prior to implantation or in the post-operative period by femtosecond laser pulses 224, as shown in FIG. 13, to create zones or regions 220 of modified refractive index for near and/or intermediate vision correction. The degree of the correction needed may be measured initially, and input into an algorithm of the software or application controlling the laser output to achieve the desired refractive change in the lens mate 200.

In some applications, multiple zones around the central aperture 216 can be created to produce a multifocal zone around the central area of the body 212 using the femtosecond laser application with desired spot size power, and frequency under automated scanning OCT for precise localization of laser application and its extent using the laser's software. The refractive error of the eye, such as astigmatism, defocus, coma, etc. may be corrected with the laser acting upon the body 212 of the mate 200 in the postoperative period. In one form, the changes in the index of refraction of the body 212 of the mate 200 is measured by a Shack-Hartmann system during the surgery.

In one method, the surface of the body 212 may be exposed to low energy nanojoule femtosecond pulses to modify the index or the refraction of the lens body 212 to the desired power and the control of a wave front technology unit to accurately provide accurate femtosecond pulses to the lens surface and create an emmetropic refraction or multifocal refraction as desired for the patient's need. In one application, prior to the implantation in the patient, the polymeric lens body 212 may be dipped in a 0.1% riboflavin or other non-toxic photosensitizers preparation to penetrate the soft polymeric plate to enhance refractive index modification or make the body 212 suitable for refractive index modification with a femtosecond laser. Alternatively, 0.05 ml riboflavin or other suitable photosensitizer agents at 0.1% concentration can be injected with a 32-34 gauge needle in the anterior chamber prior to modification of the lens mate's index of refraction during the surgery or in the postoperative period using a femtosecond laser.

In one presently preferred method, the surface of the lens body 212 may be irradiated with a femtosecond laser with a wavelength of 300 nm to 1000 nm or 350 nm-700 nm or 700 nm to 1300 nm and the energy level of 0.05 nJ to 1000 nJ or more to change the index of the refraction around the central aperture 216 rendering these areas with a higher index of refraction enhancing the reading ability combined with the increased depth of the focal or the pinhole of the transparent flexible mate 200. Alternatively, the surface of the lens body 212 polymer may be subjected to irradiation to induce changes in its index refraction around the central aperture 216.

In one preferred application, the femtosecond pulse frequency is preferably between 1 MHz to 10 or between 500 MHz to 1 GHz with a pulse length of 10 femtoseconds to 1000 femtoseconds.

In another application, the femtosecond pulse energy may range between about 0.2 nJ and about 15 nJ or greater and the focal point may be between about 0.3 micrometer and about 2 micrometers or greater. Preferably, the laser pulses scan at a speed of between about 10 mm/s to about 1000 mm/s.

Referring to FIG. 10, it will be understood that the aperture 216 in the lens mate 200 may be modified and need not be circular. For example, a lens mate 200A may be provided with a body 212A having an aperture 216A in the form of an oval or elongate slot surrounded by a darkened wall or portion of the body 212A along its perimeter. In still another form of the present invention, a lens mate 200B may be provided with a body 212B having an aperture 216B in the form of a dumbbell or infinity shape surrounded by a darkened wall or portion of the body 212B along its perimeter.

Figure 11:
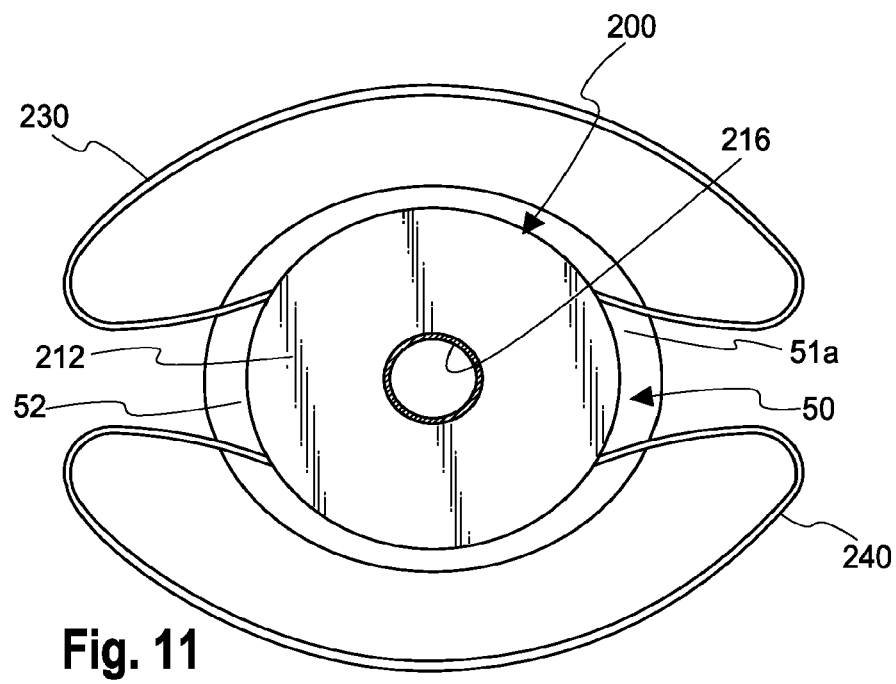
FIG. 11 illustrates a top plan view of one of the three different embodiments of the lens shown in FIG. 10 implanted overtop (anterior) of the intraocular lens of FIG. 3, and the lens mate of FIG. 11 is provided with its own haptics for stabilization within the eye.

Referring to FIG. 11, in another form of the present invention, the lens mate 200 may be provided with one or more of its own haptics 230/240 that reach the ciliary body for fixation. The haptics 230/240 of the lens mate 200 are preferably kidney-shaped, closed loops. It will be understood that the haptics 230/240 may have other shapes, such as the haptics 51a and 51b of the IOL 50, or may be cantilevered arms that are not in form of loops.

The inventors of the present invention intend that the lens mate 200 and the primary IOL may be mounted and then implanted in the eye with viscoelastic fluid such as hyaluronic acid through an injector. Alternatively, the IOL may be implanted first, followed by the separate implantation of the lens mate 200 by way of a plunger type injector, as is known in the art. The lens mate 200 and the primary IOL, such as the IOL 50 or any prior art IOL, may be connected or spaced from each other at all times. The lens mate 200 is designed to be easily removed or replaced as needed in the postoperative period through a sub-2 mm incision under topical anesthesia under a slit-lamp observation.

Figure 12:
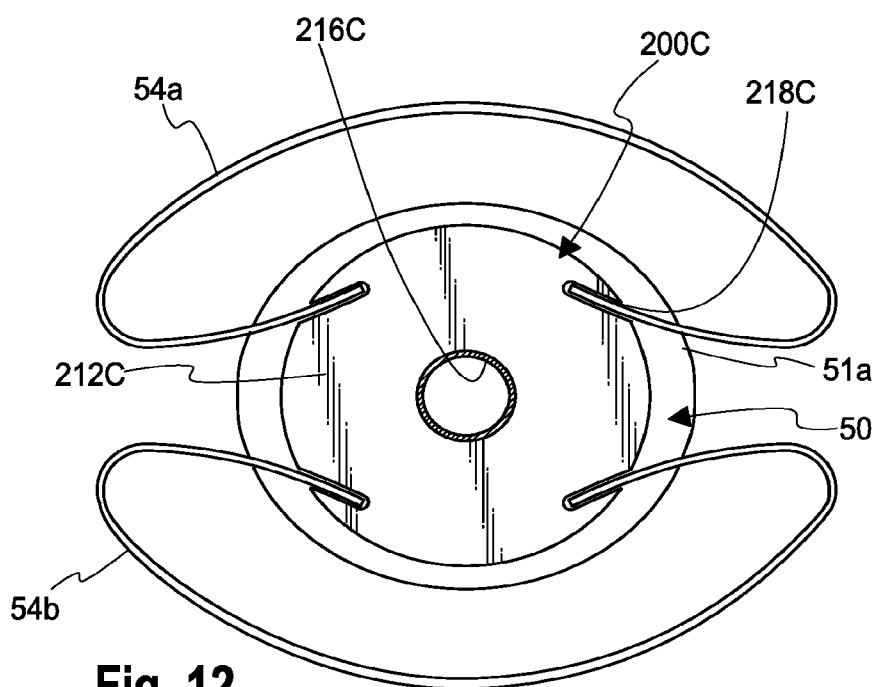
FIG. 12 illustrates a top plan view of another embodiment of a lens mate shown implanted over an intraocular lens.

With reference now to FIG. 12, a lens mate 200C may be provided with a lens body 212C, aperture 212C, and a plurality of U-shaped cutouts or channels 218C in the periphery of the body 212C that capture or mechanically engage the haptics of the primary IOL, such as the haptics 54a/54b of the aforementioned IOL 50 as illustrated. The engagement of the lens mate 200C with the primary IOL prevents substantial relative motion between the two bodies when implanted in the eye as shown in FIG. 12.

It will be understood that the laser or irradiation-based techniques described above for modification of the refractive index of the mate 200 may be suitably used for the other embodiments of the mate 200A, 200B, 200C described and/or illustrated.

Figure 14:
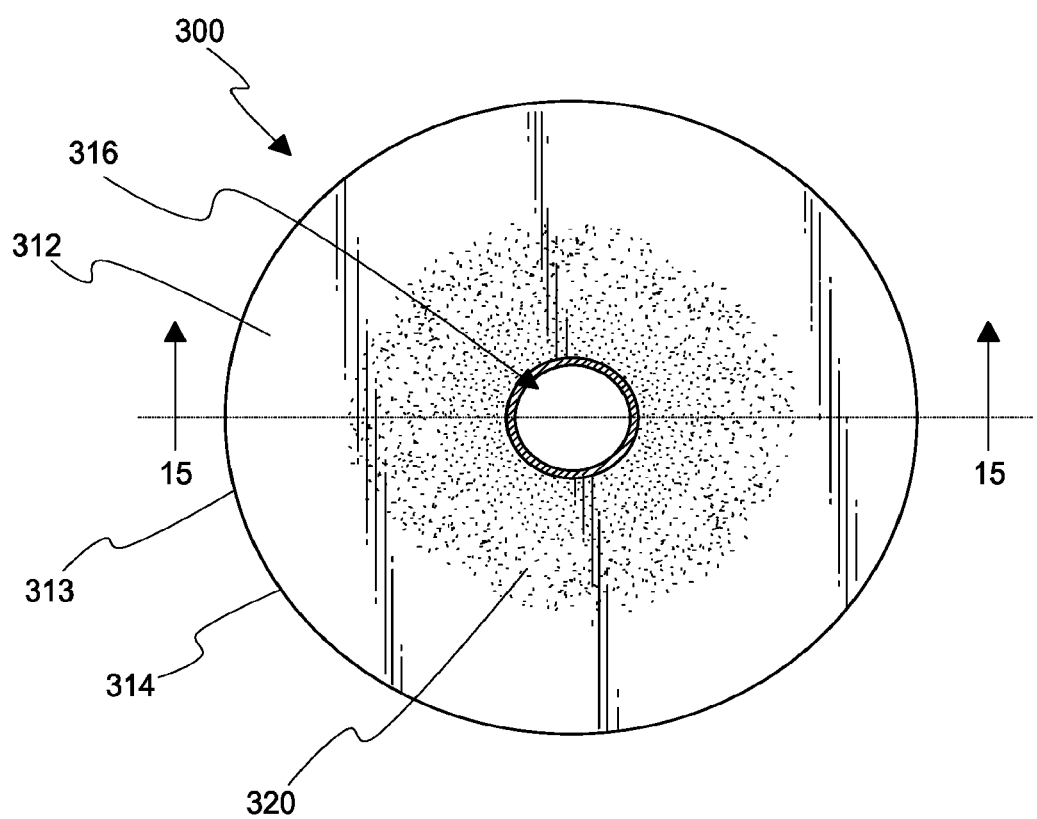
FIG. 14 illustrates a top plan view of another embodiment of a refractive lens or a lens mate according to the present invention, and FIG. 14 omits the haptics of the lens for illustrative purposes.
Figure 15:
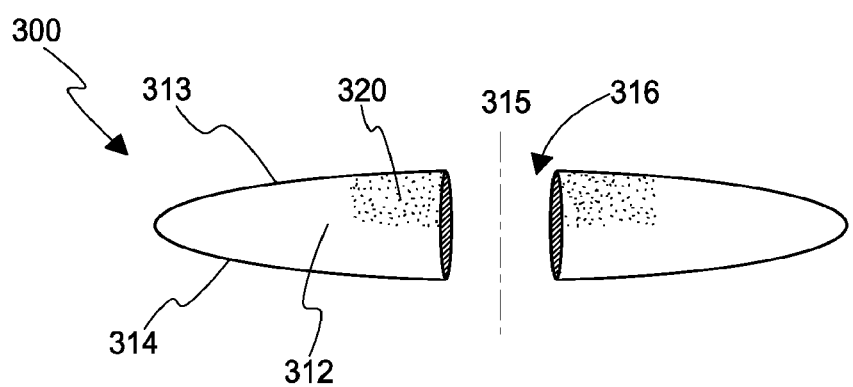
FIG. 15 illustrates a cross-sectional view of the lens of FIG. 14 taken along view line 15-15 in FIG. 14.
Figure 18:
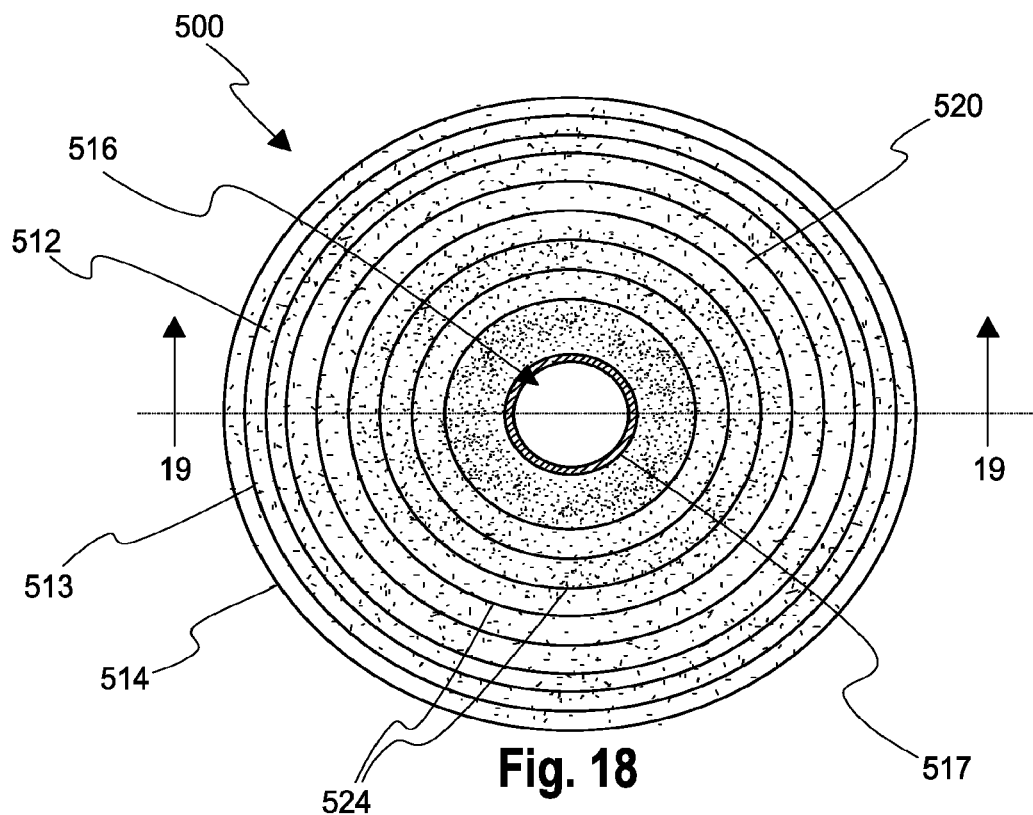
FIG. 18 illustrates a top plan view of another embodiment of a diffractive lens or a lens mate according to the present invention, and FIG. 18 omits the haptics of the lens for illustrative purposes.
Figure 19:
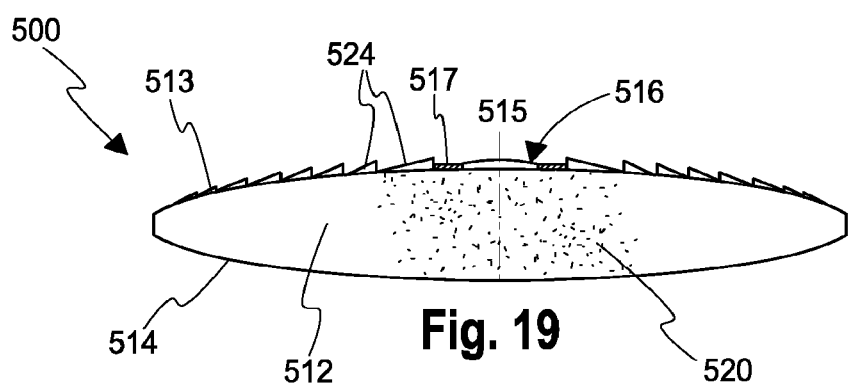
FIG. 19 illustrates a cross-sectional view of the lens of FIG. 18 taken along view line 19-19 in FIG. 18.
Figure 20:
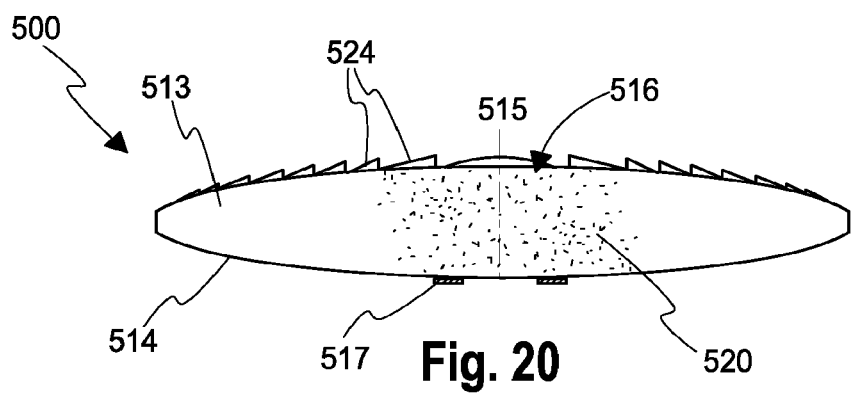
FIG. 20 illustrates a cross-sectional view of the lens of FIG. 18 taken along view line 19-19 in FIG. 18.

With reference now to FIGS. 14 and 15, another embodiment of a lens according to the present invention is illustrated and designated by the numeral 300. The lens 300 includes a central lens body 312 that has the form of a refractive lens and shaped to provide correction to the eye and may be provided with one or more haptics (not illustrated, but as described above with respect to the other embodiments). The lens body 312 defines a curved anterior surface 313 and a posterior surface 314 with an optical axis 315 extending between the surfaces 313 and 314.

The central lens body 312 may be provided alone, for correction of the eye, or may be provided as discussed above in the form lens mate for being implanted over, i.e., in front of, or anterior to, an implanted intraocular lens, such as the aforementioned lens 50 or a commercially available prior art IOL.

The lens body 312 includes a central through hole or aperture 316 that may be between about 1.0 and about 3.0 mm in diameter. The aperture 316 is surrounded by a darkened portion of the lens body 312 or interior wall along its perimeter to prevent or minimize light scattering, and rendering a pin hole effect to the light by extending the focal point area for the near objects and focusing on the distant objects for a patient. In one preferred form, the aperture 316 is defined by a three-dimensional configuration passing from the front surface of the lens 300 to the back surface of the lens with darkened side walls, therebetween, to prevent light scattering and the light that passes through the pinhole is in focus for the objects located in the far or near continuously, enhancing the depth of focus for any distance and thus improves the depth of perception in a standard, refractive lens. The darkened material of the aperture 316 may be a paint or coating on the lens body 312 to prevent leakage of light.

The lens 300 is preferably formed from one or more semi-flexible, flexible, or foldable transparent polymeric materials such as PMMA, acrylic, silicone, hydrogel, or combination of silicone hydrogel or crosslinked collagen or elastin, etc. such that the body 312 index of refraction may be modified non-invasively by using a femtosecond laser as needed throughout the patient's life. In some applications, the lens 300 has a fixed refractive power. However, the refractive index of the lens 300 preferably is modified in a region or zone 320 surrounding the aperture 316 to create bifocal, trifocal, multifocal or toric lens prior to the surgery or afterward using nanojoule pulses of a femtosecond laser applied to the anterior surface 313 of the body 312 as discussed above. The body 312 may be provided with an extra soft polymeric surface such as crosslinked collagen. The refractive power of the lens body 312 is corrected as needed, prior to implantation or in the post-operative period by femtosecond laser pulses, to create one or more zones or regions 320 of modified refractive index for near and/or intermediate vision correction. The degree of the correction needed may be measured initially, and input into an algorithm of the software or application controlling the laser output to achieve the desired refractive change in the lens 300.

Figure 24:
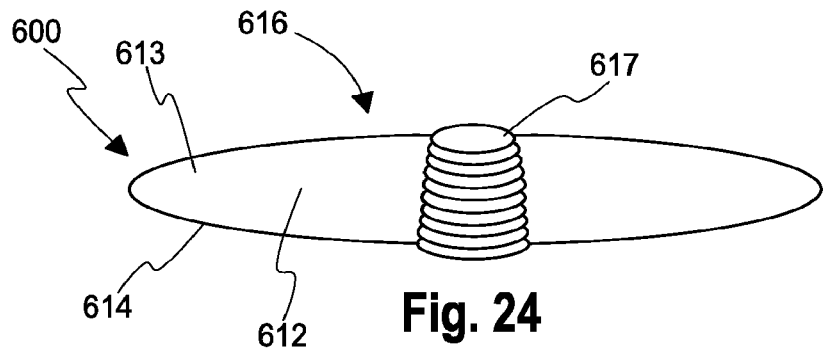
FIG. 24 illustrates a cross-sectional view of the lens of FIG. 21 taken along view line 23-23 in FIG. 21.
Figure 25:
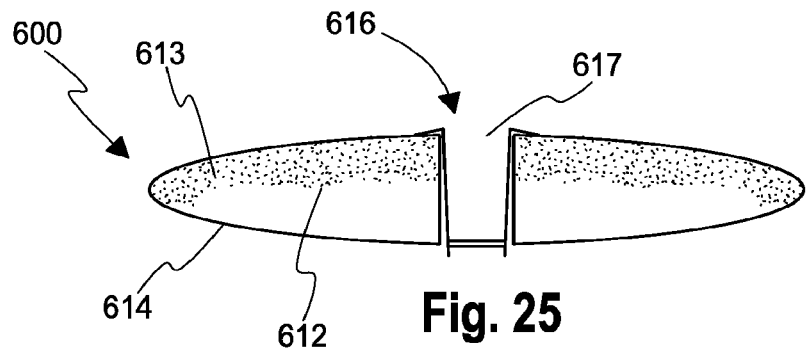
FIG. 25 illustrates a cross-sectional view of the lens of FIG. 21 taken along view line 23-23 in FIG. 21.
Figure 32:
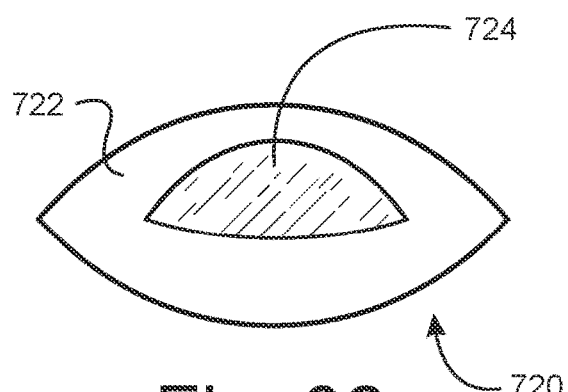
FIG. 32 illustrates a cross-sectional view of yet another embodiment of an intraocular lens where an internal convex portion has been formed inside the intraocular lens using a femtosecond laser.
Figure 33:
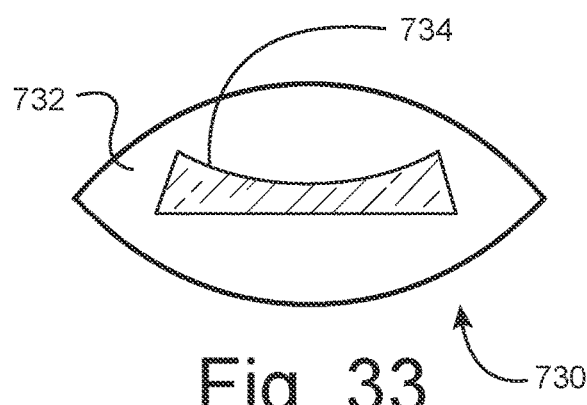
FIG. 33 illustrates a cross-sectional view of still another embodiment of an intraocular lens where an internal concave portion has been formed inside the intraocular lens using a femtosecond laser.
Figure 34:
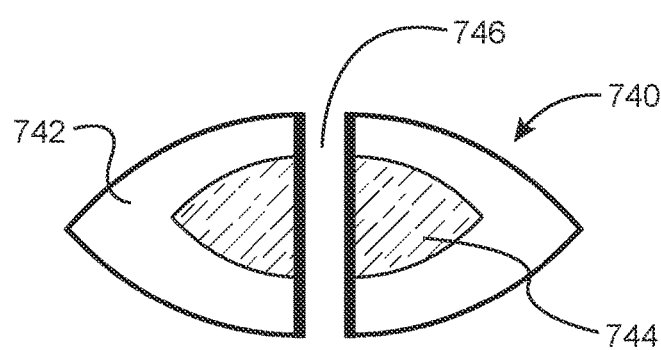
FIG. 34 illustrates a cross-sectional view of yet another embodiment of an intraocular lens with a central aperture surrounded by a darkened wall where an internal convex portion has been formed inside the intraocular lens using a femtosecond laser.

In another embodiment, the femtosecond laser creates a dense area with a higher index of refraction and/or the intraocular lens (IOL) has a lens front surface that is concave or convex, or has a surface that is concave or convex inside the IOL, thus, one can increase or decrease the dioptric power of the entire IOL, or the dioptric power of a first portion of the IOL can be increased or decreased, while a second portion of the IOL can be neutral (see FIGS. 32-24). In FIG. 32, an intraocular lens 720 has a convex portion 724 formed inside the lens body 722 by using a femtosecond laser so as to form a positive lens. In FIG. 33, an intraocular lens 730 has a concave portion 734 formed inside the lens body 732 by using a femtosecond laser so as to form a negative lens. In FIG. 34, an intraocular lens 740 with a central aperture 746 surrounded by a darkened wall has a convex portion 744 formed inside the lens body 742 by using a femtosecond laser.

In yet another embodiment, a collamer lens with a central through hole surrounded by a darkened wall is placed in the eye via a small incision through the limbus, through the pupil, in front of a transparent natural crystalline lens, and behind the iris with a standard lens implantation technique. The collamer lens of this embodiment is provided with haptics to reach to the ciliary body so as to stabilize the lens, and to correct the refractive power of the eye and extend the focal point of the natural crystalline lens from a far to near point continuously while correcting the refractive error.

In still another embodiment, a collamer lens with a central through hole surrounded by a darkened wall is placed in the eye via a small incision through the limbus, through the pupil, in front of an existing intraocular lens (IOL), and behind the iris with a standard lens implantation technique. The collamer lens of this embodiment is provided with haptics to reach to the ciliary body so as to stabilize the lens, and to correct the refractive power of the eye and extend the focal point of the existing intraocular lens from a far point to a near point continuously, while correcting the refractive error.

Figure 31:
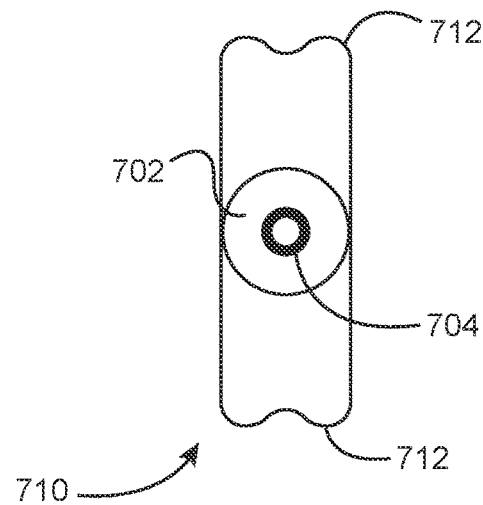
FIG. 31 illustrates a top plan view of still another embodiment of an intraocular lens with a central aperture surrounded by a darkened wall and haptics designed for placement of the intraocular lens inside the posterior chamber behind the iris.

An illustrative embodiment of a collamer lens 710 with a central aperture surrounded by a darkened wall 704 is illustrated in FIG. 31. This collamer lens 710 is configured to be placed in the posterior chamber of the eye behind the iris. As described above, the collamer lens may be placed in front of a transparent natural crystalline lens or in front of an existing intraocular lens in the eye. As shown in FIG. 31, the collamer lens 710 further includes haptics 712 extending outwardly from the lens body 702 so that the collamer lens 710 is properly centered and stable when inserted in the posterior chamber of the eye behind the iris.

In one presently preferred embodiment, the lens 300 with a central aperture 316 provides an increased depth of focus and by adjusting the index of refraction in the area 320 around the central aperture 316 to focus the light over the fovea using a femtosecond laser pulses under the control of a software and wave front technology. It is believed that this embodiment will enhance the desired far or near vision while the central hole enhances the depth of focus.

Figure 26:
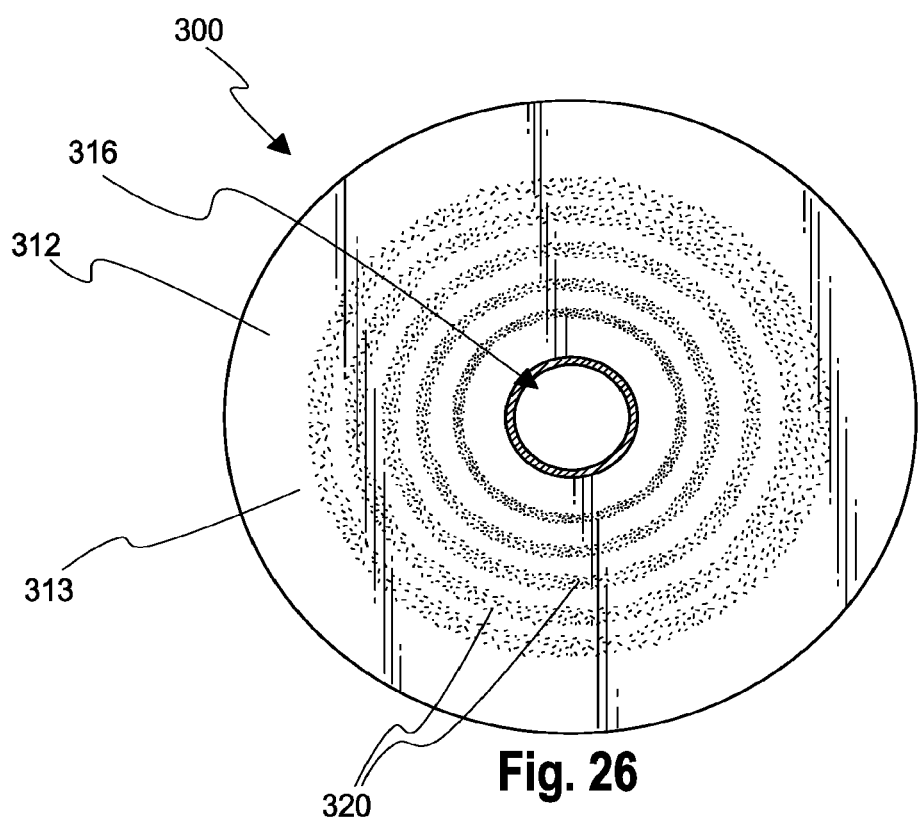
FIG. 26 illustrates a top plan view of another embodiment of a refractive lens or a lens mate according to the present invention, and FIG. 26 omits the haptics of the lens for illustrative purposes.

In another embodiment, illustrated in FIG. 26, the standard monofocal pinhole lens 300 can be converted to bifocal, trifocal or quadri-focal, etc., lens by changing only the index of the refraction in a plurality of concentric zones 320 around the central hole continuously to the periphery of the lens body 312 without changing the smooth anterior surface 313 of the lens 300, thereby creating a multifocal lens 300 that does not have height and valley on its surface as with a diffractive lens. The lens 300 preferably has a substantially invisible transition between each zone 320 such that the index of refraction changes occurs gradually below the lens anterior surface 313 after femtosecond laser application, and does not cause any ridges on the lens surface such that it does not cause the light to scatter such as by the incoming traffic light, at night, etc.

Figure 27:
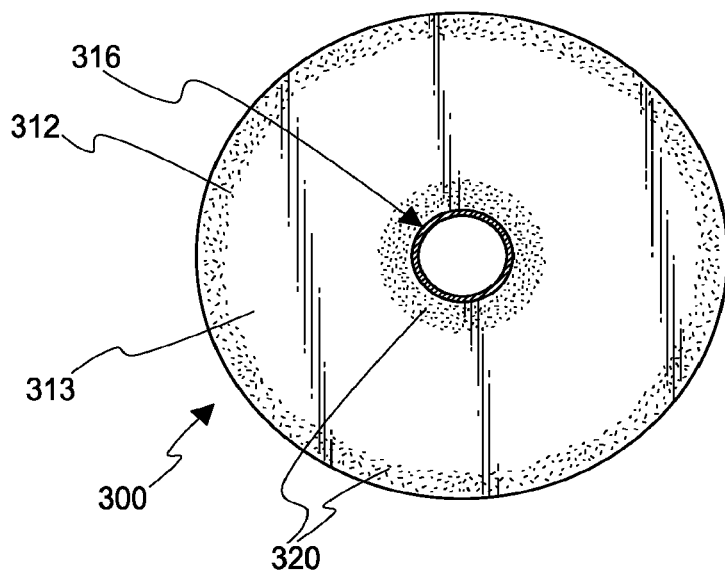
FIG. 27 illustrates a top plan view of another embodiment of a refractive lens or a lens mate according to the present invention, and FIG. 27 omits the haptics of the lens for illustrative purposes.

In one embodiment, illustrated in FIG. 27, the lens 300 can have a first zone 320 for correction of the index of refraction near the central hole to a desired dioptric power for near or far distance and the peripheral part of the lens has a second zone 320 corrected for the peripheral light rays passing through the peripheral pupil to fall on the retina which is located at a closer distance to the lens 300, thus providing a more "in focus", expanded panoramic image for the peripheral retina and/or correcting the spherical and chromatic aberrations using a femtosecond laser pulses.

In one embodiment, using a femtosecond laser alters the refractive index of lens 300 on a point-by-point basis to generate the desired refractive profile.

In yet another embodiment of the invention, the central aperture 316 of the lens 300 reduces the lower or higher order of aberration and astigmatic changes of the cornea because only the central light beam passes through the central aperture 316, thereby it contributes toward an improved visual perception for near and far objects.

Figure 28:
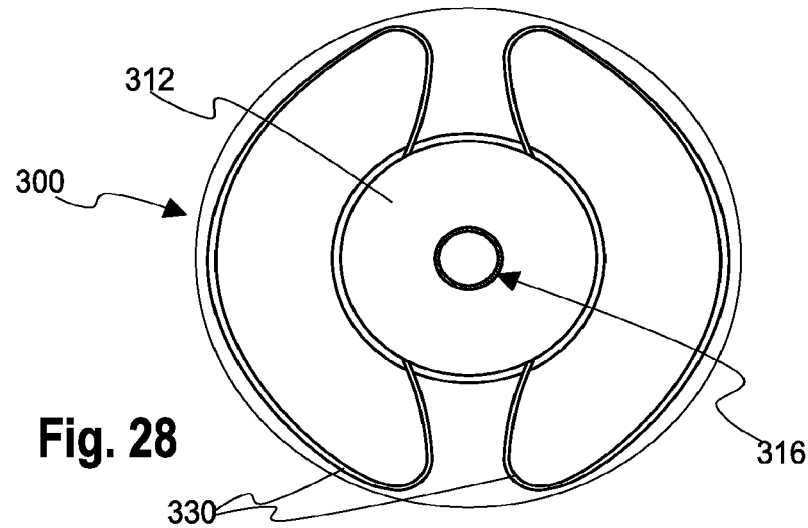
FIG. 28 illustrates a top plan view of another embodiment of a lens or a lens mate according to the present invention implanted within the eye.
Figure 29:
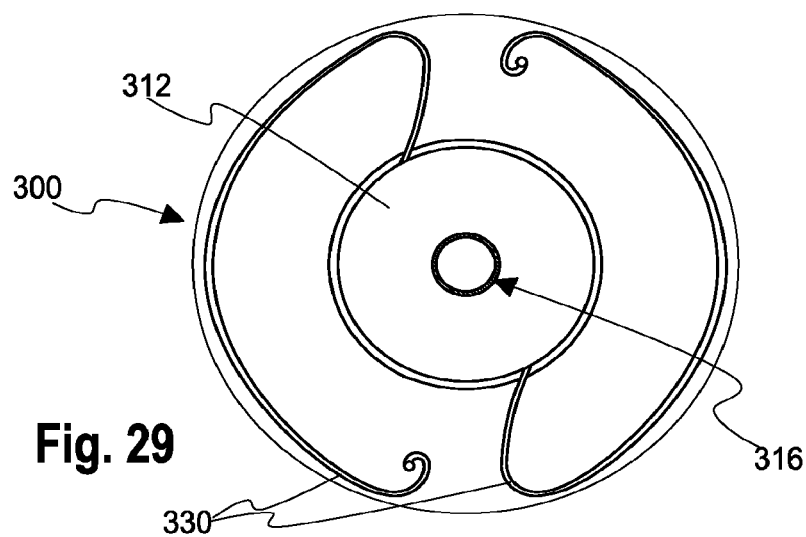
FIG. 29 illustrates a top plan view of the lens of FIG. 28 implanted in the eye.

In yet another embodiment, the lens body 312 is attached to a standard but preferably a large sized haptic or a cut/cantilevered haptic 330 (FIGS. 28 and 29) to fill the capsular bag so that the lens is properly centered and stable in the capsular bag and the edges of the lens body 312 are made squared to prevent capsular opacification, by preventing migration of remaining sub-capsular lens cells. FIGS. 28 and 29 show the lens 300 in two haptic configurations within the capsular bag of the eye, wherein the anterior edge of the capsular bag overlies a substantial portion of the lens body 312.

Figure 30:
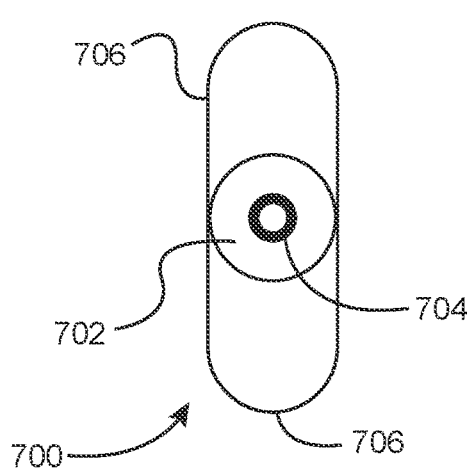
FIG. 30 illustrates a top plan view of yet another embodiment of an intraocular lens with a central aperture surrounded by a darkened wall and haptics designed for placement of the intraocular lens inside the lens capsule.

In still another embodiment, with reference to FIG. 30, an intraocular lens 700 that is configured to be placed in the lens capsule of an eye has a lens body 702 with a central aperture surrounded by a darkened wall 704. As shown in FIG. 30, the intraocular lens 700 further includes haptics 706 extending outwardly from the lens body 702 so that the intraocular lens 700 is properly centered and stable when inserted into the lens capsule.

With reference now to FIGS. 16 and 17, another embodiment of a lens according to the present invention is illustrated and designated by the numeral 400. The lens 400 includes a central lens body 412 that has the form of a diffractive lens and shaped to provide correction to the eye and may be provided with one or more haptics (not illustrated, but as described above with respect to the other embodiments). The lens body 412 defines an anterior surface 413 and a posterior surface 414 with an optical axis 415 extending between the surfaces 413 and 414.

The central lens body 412 may be provided alone, for correction of the eye, or may be provided as discussed above in the form lens mate for being implanted over, i.e., in front of, or anterior to, an implanted intraocular lens, such as the aforementioned lens 50 or a commercially available prior art IOL.

The lens body 412 includes a central through hole or aperture 416 that may be between about 1.0 and about 3.0 mm in diameter. The aperture 416 is surrounded by a darkened portion of the lens body 412 or interior wall along its perimeter to prevent or minimize light scattering, and rendering a pin hole effect to the light by extending the focal point area for the near objects and focusing on the distant objects for a patient. In one preferred form, the aperture 416 is defined by a three-dimensional configuration passing from the front surface of the lens 400 to the back surface of the lens with darkened interior or side walls, therebetween, to prevent light scattering and the light that passes through the pinhole is in focus for the objects located in the far or near continuously, enhancing the depth of focus for any distance and thus; improves the depth of perception in a diffractive lens. It is believed that the central aperture 416 improves the visual perception in the multifocal embodiment of the diffractive lens 400 for any distance because the central beams are always in focus while observing simultaneously the different focal points of a diffractive lens because the final visual perception is constructed in the brain somewhat like computer software accepting the "in focus light rays" while eliminating those that are not "in focus" creating a desirable sharp image for the patient.

The lens 400 is preferably formed from one or more semi-flexible, flexible, or foldable transparent polymeric materials such as PMMA, acrylic, silicone, hydrogel, or combination of silicone hydrogel or crosslinked collagen or elastin, etc. such that the body 412 index of refraction may be modified non-invasively by using a femtosecond laser as needed throughout the patient's life. In this application, the lens 400 has a fixed diffractive power. However, in another application the inventive method corrects the remaining refractive power of the lens 400 prior or preferably after a period of time in the postoperative period using a femtosecond laser by changing the index of the refraction of the central area or region 420 of the diffractive lens as described above with respect to the refractive lenses. In one embodiment, the precentral central circular area 420 around the central aperture 416 is modified for near vision while in another embodiment the precentral circular area 420 around the central aperture 416 is corrected for far vision depending on the preference of the patient for a sharper near or far vision. It is believed that both configurations should work for most of the patients to have at least 20/20 vision or 20/25 vision with an extended depth of focus created by the pinhole effect of the aperture 416. In one embodiment, a diffractive multifocal lens 400 is configured to provide simultaneous near and distance.

Figure 21:
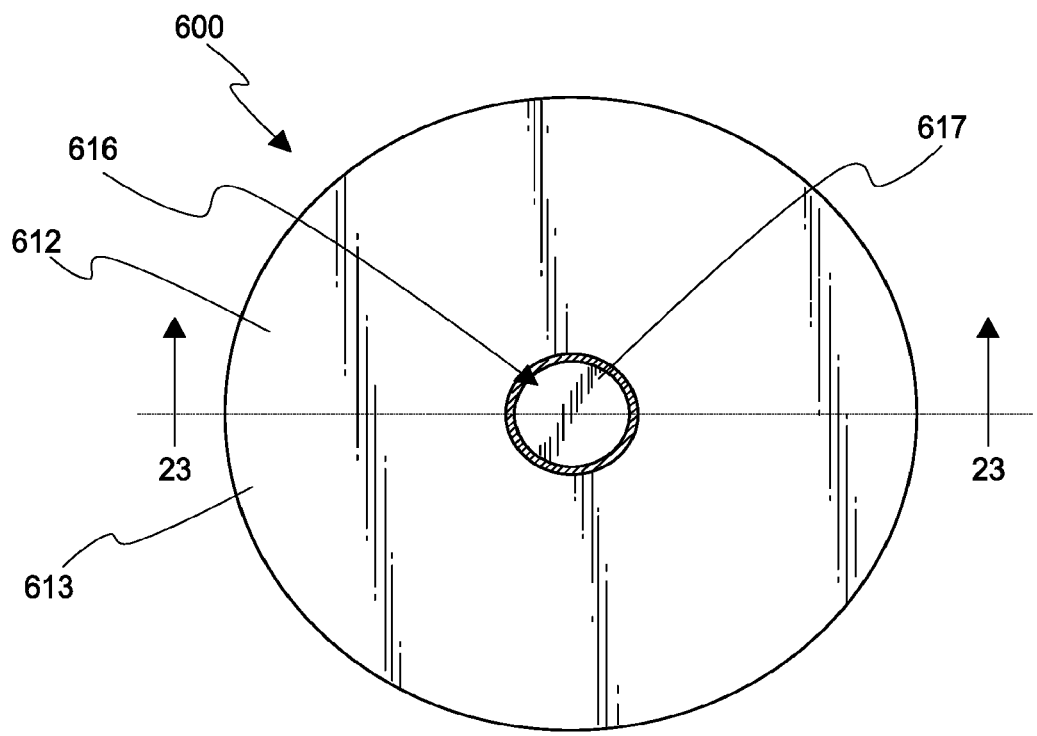
FIG. 21 illustrates a top plan view of another embodiment of a refractive lens or a lens mate according to the present invention, and FIG. 21 omits the haptics of the lens for illustrative purposes.
Figure 22:
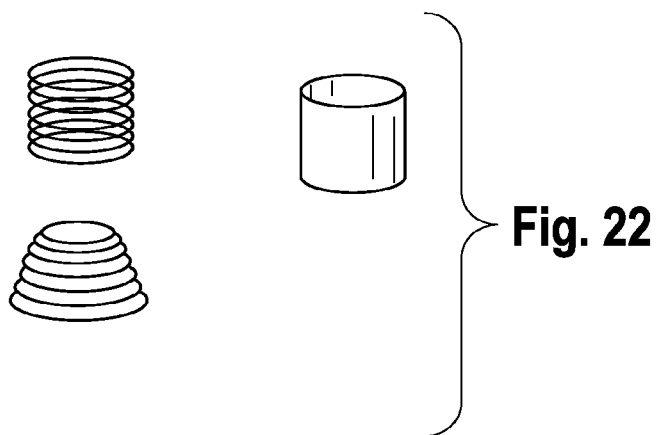
FIG. 22 illustrates several variations of plug members in an isometric view, taken from above.
Figure 23:
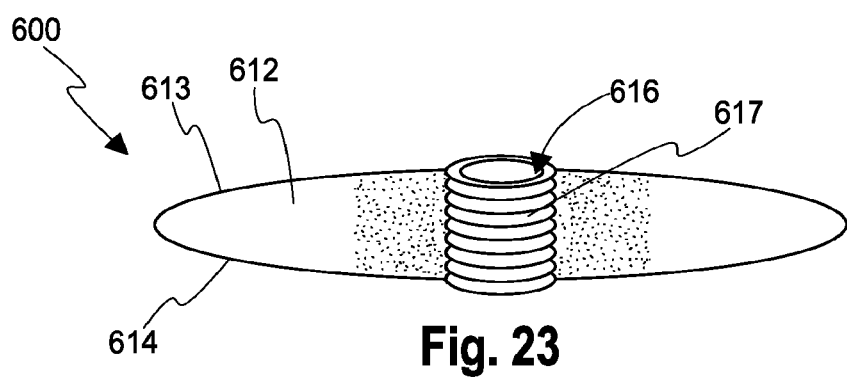
FIG. 23 illustrates a cross-sectional view of the lens of FIG. 21 taken along view line 23-23 in FIG. 21.

With reference now to FIGS. 21 and 22, another alternative embodiment of a lens according to the present invention is illustrated and designated by the numeral 600. The lens 600 includes a central lens body 612 that has the form of either a refractive or diffractive lens and shaped to provide correction to the eye and may be provided with one or more haptics (not illustrated, but as described above with respect to the other embodiments). The lens body 612 defines an anterior surface 613 and a posterior surface 614 with an optical axis 615 extending between the surfaces 613 and 614.

The central lens body 612 may be provided alone, for correction of the eye, or may be provided as discussed above in the form lens mate for being implanted over, i.e., in front of, or anterior to, an implanted intraocular lens, such as the aforementioned lens 50 or a commercially available prior art IOL.

The lens body 612 includes an aperture 616 that is configured to receive an insert or plug member 617, in the form of an assembly, wherein the interface between the plug member 617 and the body 612 provides the darkened perimeter of the aperture 616 to prevent or minimize light scattering. With reference to FIG. 22, the plug member 617 may have a variety of forms, such as a cylindrical spring, a conical spring, a solid cylindrical plug, a solid frustoconical plug, a hollow plug, etc. The plug member 617 may take other shapes sufficient to establish a darkened perimeter of the aperture 616, and may be an adhesive, bi-injection molded element, friction fit element, welded element, etc. The plug member 617 may be a polymer or metallic material to provide a thin darkened surface that does not reduce light passing through the lens and does not reduce night vision, but which blocks light that is outside of the aperture 616 from entering. In one preferred form, the lens body 612 has a diameter of between about 5 and 7 mm, preferably 6 mm, and the central area is drilled, molded, lasered to produce a through hole or aperture 616 of between about 2-3 mm in diameter. In this preferred embodiment, the cylinder or cone shaped plug member 617 having a darkened peripheral wall is received within the aperture 616 to reduce glare.

In one preferred embodiment of the lens 200, 300, 400, 500, or 600, a femtosecond refractive index correction in the central area of 2-3 mm area is made post-operatively to achieve a change in the refractive index of the lens 200, 300, 400, 500, or 600 and provide a broader area for presbyopia correction and of the peripheral remaining zone of the lens which is gradually corrected to provide the peripheral rays to focus on the peripheral retina to create a sharper and wider peripheral image using a femtosecond laser.

In another preferred embodiment of the lens 200, 300, 400, 500, or 600, a femtosecond refractive index correction is made preoperatively or in the postoperative period one any remaining refractive errors such as astigmatism, spherical and chromatic aberrations of the eye as a whole expanding the correction to the peripheral area to provide more in-focus light beam for the peripheral retina.

In another preferred embodiment of the lens 200, 300, 400, 500, or 600, a femtosecond refractive index correction is made around the aperture for either myopic correction of the lens around the central hole preoperatively or in the postoperative period correcting the remaining refractive aberrations around the central hole as needed for presbyopia and or for hyperopia to achieve 20/20 vision for near or far vision using a femtosecond laser.

According to yet another presently preferred embodiment, the diameter of the haptic of the lens 200, 300, 400, 500, or 600 reaches a diameter of between 12 and 14 mm, preferably 13 mm or more, to fill the diameter of capsular bag preventing its collapse after lens implantation. The initial refractive power of the lens 200, 300, 400, 500, or 600 can be changed after implantation in the postoperative period.

In another preferred embodiment of the lens 200, 300, 400, 500, or 600, a femtosecond refractive index correction is made to the paracentral area of the lens body outside the for near or far vision as needed, so that the lens can be made to result a 20/20 vision in the far vision or for presbyopia before or near after implantation of the lens with a femtosecond laser pulses. It is believed that this lens embodiment will prevent dysphotopsias when the cornea has a surface irregularities.

In still another embodiment of the lens 200, 300, 400, 500, or 600, the haptic ends close to the lens body may be brought together to fill the capsular bag so that the lens body does not move after surgery and the center of the aperture locates in the center of the visual axis of the patient's eye.

In another preferred embodiment of the lens 200, 300, 400, 500, or 600, the lens material is hydrophobic, however its surface can be changed to hydrophilic with femtosecond laser pulses as needed.

In another preferred embodiment of the lens 200, 300, 400, 500, or 600, the lens is combined with a standard multifocal IOL, whereby a pinhole aperture provides a combination lens so as to provide a multifocal lens with extended focus for any distance from the eye.

According to another preferred embodiment of the lens 200, 300, 400, 500, or 600, the central area of a monofocal lens body can be corrected with femtosecond laser so that it is made myopic of −1.00 to −1.5 diopter or more for near vision for the patient before or after implantation. In this embodiment, a central aperture is drilled, or otherwise molded or formed, in the lens body to provide an extended depth of focus for the near vision and improve the far vision for these types of lenses. An additional adjustment can be made in the postoperative period if needed.

In another preferred embodiment of the lens 200, 300, 400, 500, or 600 the index of refraction of an area of the lens body can be divided as follows: 20% of the anterior surface for bifocal, 40% of the anterior surface for near focus, and 40% of the anterior surface area for far focus to create a trifocal lens with a central aperture using a molding technique or surface ablation or modifying their index of refraction with femtosecond laser preoperative or afterward to create a bifocal or trifocal IOL without producing ridges on the lens surface.

In still another form of the present invention, in the postoperative period, one can simultaneously correct the remaining refractive errors such as spherical, astigmatism, chromatic aberrations or expanding the correction to the peripheral area of the lens 200, 300, 400, 500, or 600 to provide a more in-focus light beam for the peripheral retina.

In some applications, the body of the lens 200, 300, 400, 500, or 600 may be made from acrylic, hydrogel, and other transparent polymeric materials, or is made aspherical. The anterior surface of the lens body may be sprayed with a nanoparticle composition to produce a nanostructured surface which serves as an alternative to thin-film antireflection coatings. The lens body may be provided with an ultraviolet absorbing material.

In the event of prior injury to the crystalline lens, the body of the lens 200, 300, 400, 500, or 600 can be placed in the sulcus behind the iris. The lens 200, 300, 400, 500, or 600 can be implanted in children after traumatic cataract or congenital cataract surgery because the central aperture provides an in-focus view of far and near objects and the lens body index of refraction can be modified at any time, when the eye grows without the need of removing or replacing the IOL surgically. The refractive power of the lens can be adjusted in children with traumatic lens injury.

In one embodiment of the present invention, the extreme peripheral portion (i.e., the radially or laterally outermost portion relative to the optical axis) of the lens can also be corrected to bring light in focus for the peripheral retina, therefore widening the field of the view of the eye.

In one embodiment of the present invention, the lens 200, 300, 400, 500, or 600 can be used for monocular or binocular correction because it does not limit significantly the light reaching the retina. This is because the darkened area around the central aperture is thin and covers the entire surface area of the aperture or the full thickness of the central aperture. This structure also simplifies the unobstructed view of the retina such as in retinal surgery.

Now, various surgical procedures using an optical implant in the treatment of a congenital cataract will be described hereinafter. In one embodiment of cataract extraction and intraocular (IOL) implantation, one calculates the IOL power needed, under anesthesia, with evaluation of the anterior chamber, intraocular pressure (IOP), corneal diameter, gonioscopy, axial length measurement (17-17.5 mm), and refractive status of both eyes are measured and myopic shift is considered, since the eyes grow rapidly at ages <1 year. The initial surgery is done with an under correction 10-29% power using an aberrometer to calculate the IOL power with a formula such as Holladay or SRK/T for the best prediction with the goal of creating a post-operative hyperopia.

In one embodiment, the standard preoperative examination includes a complete blood count (CBC) test, a title of viral infections, blood sugar test, red cell galactokinase, urine analysis, and DNA sequencing.

In one embodiment, the non-surgical therapy includes frequent monitoring the eyes to prevention amblyopia, and medication may be given to increase the size of the pupil so that the patient can see around the lens opacity.

In one embodiment, the indications for cataract extraction in babies are the size of the central lens opacity >3 mm, strabismus, and/or nystagmus. The surgery is more complicated if done before 6 weeks of age, since general anesthesia needs to be used.

Figure 35:
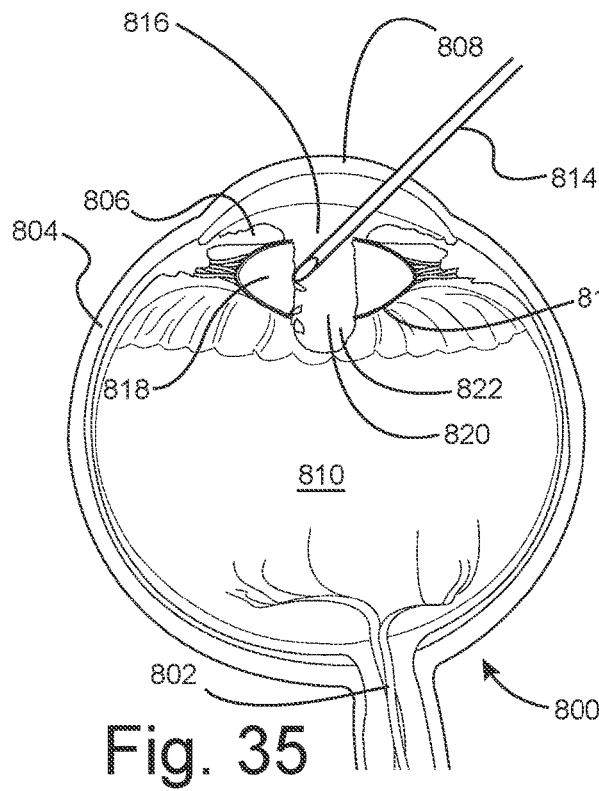
FIG. 35 is an enlarged, diagrammatic cross-sectional view of a human eye undergoing a surgical procedure that includes the removal of a natural lens, the forming of anterior and posterior openings in the capsular bag, and the removal of vitreous material behind the posterior opening in the capsular bag, wherein the surgical instrument performing the surgical procedure is inserted through an anterior portion of the eye.

In one embodiment, the lensectomy is performed through the limbus, followed with an anterior capsulotomy, removal of the lens cortex followed with central posterior capsulotomy, and an anterior vitrectomy (see e.g., FIG. 35).

In one embodiment, the lensectomy is performed through the limbus followed with anterior capsulotomy, removal of the lens cortex followed by central posterior capsulotomy leaving the anterior hyaloid membrane intact (see e.g., FIG. 35), while infusing viscoelastic in the anterior chamber or in the lens capsule, then implanting a pinhole lens in the capsular bag or capturing the posterior capsule with the intraocular (IOL) having a central pinhole with a darkened wall, or using a haptic to capture the posterior capsule, irrigating the lens, and remove the viscoelastics, and preventing capsular opacification.

In one embodiment, a pars plana or pars plicata approach is used to insert a vitrectomy instrument performing an anterior vitrectomy and/or a complete vitrectomy, followed with a posterior lens capsulotomy and removal of the lens cortex, followed with removal of a central anterior capsule from its backside (see e.g., FIG. 37), keeping the infusion pressure to maintain pressure in the eye making a limbal corneal incision and implanting a pinhole lens inside the capsule.

In one embodiment, the capsulotomy can be done with a femtosecond laser to the posterior capsule (see e.g., FIGS. 35-37) or anterior capsule for the atraumatic removal with forceps prior to the removal of the lens cortex or nucleus and thus, as a result of the less traumatic surgery, less inflammation is produced after the surgery. However, even though vitrectomy can be limited to the anterior vitreous, the more vitreous that is removed, the less complications that are encountered in the post-operative period, such as inflammation leading to scar formation. The administration of anti-inflammatory agents inside the eye helps fight the inflammatory response or the glaucoma, two of the major complications after cataract extraction in children.

Figure 36:
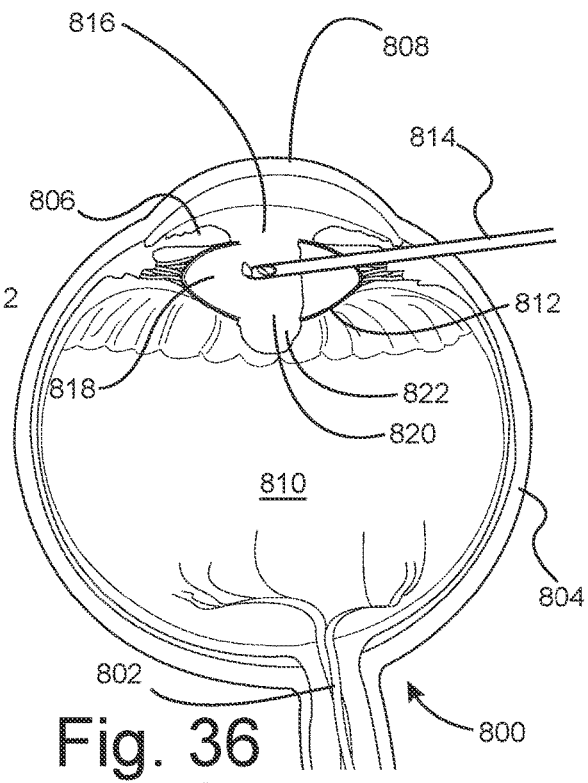
FIG. 36 is an enlarged, diagrammatic cross-sectional view of a human eye undergoing a surgical procedure that includes the removal of a natural lens, the forming of anterior and posterior openings in the capsular bag, and the removal of vitreous material behind the posterior opening in the capsular bag, wherein the surgical instrument performing the surgical procedure is inserted through a first posterior portion of the eye (e.g., through the pars plicata)
Figure 37:
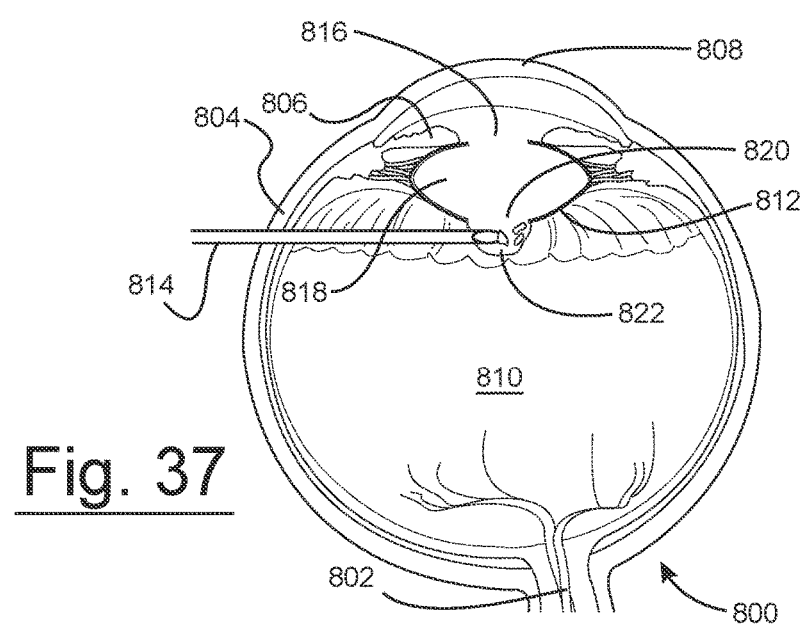
FIG. 37 is an enlarged, diagrammatic cross-sectional view of a human eye undergoing a surgical procedure that includes the removal of a natural lens, the forming of anterior and posterior openings in the capsular bag, and the removal of vitreous material behind the posterior opening in the capsular bag, wherein the surgical instrument performing the surgical procedure is inserted through a second posterior portion of the eye (e.g., through the pars plana)

Now, with reference to FIGS. 35-37, example surgical procedures performed on the eye 800 prior to the implantation of a pinhole-type intraocular lens will be described. As shown in these figures, the eye 800 includes optic nerve 802, sclera 804, iris 806, cornea 808, vitreous cavity 810, and capsular bag 812. In FIG. 35, the vitrectomy instrument 814 is initially inserted through the limbus, then an anterior capsulotomy 816 is performed, the lens cortex and nucleus 818 is removed, a central posterior capsulotomy 820 is performed, and finally the vitreous material around the posterior hole in the capsular bag is removed 822. In FIG. 36, the vitrectomy instrument 814 is initially inserted through the pars plicata, the lensectomy 818 is performed, followed by an anterior capsulotomy 816, followed by central posterior capsulotomy 820, and finally an anterior vitrectomy 822. In FIG. 37, the vitrectomy instrument 814 is initially inserted through the pars plana, an anterior vitrectomy 822 is performed, followed with a posterior lens capsulotomy 820 and removal of the lens cortex and nucleus 818, followed by removal of a central anterior capsule 816 from its backside.

Congenital cataract removal followed by implantation of a conventional intraocular lens (IOL) in the lens capsule produces unsatisfactory results when the eye continues grow in children, and results in requiring a different refractive power that cannot be corrected with the implanted IOL. Therefore, objects are not in focus for both the near and far vision of the child. Thus, within a few years after implantation of the IOL, the child could not see objects in focus for far or near.

In one embodiment, an intraocular lens (IOL) with an annular mask forming a virtual pinhole or a lens with a central pinhole with a darkened wall is implanted in the eye of the child. The pinhole lenses have the advantage that the objects in front of the eye are always in focus for a far distance, a near distance, or an intermediate distance (e.g., refer to FIGS. 38-43). In one embodiment, a surgery can be performed with a lens having pinhole, or a lens having a virtual pinhole created by a mask to provide far and near vision for the patient and the periphery of the lens can be corrected for a dioptric power needed depending on the axial length of the eye.

Figure 38:
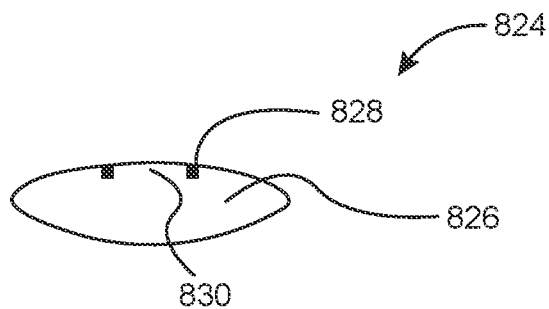
FIG. 38 illustrates a cross-sectional view of still another embodiment of an intraocular lens with a virtual pinhole formed by an annular mask.
Figure 39:
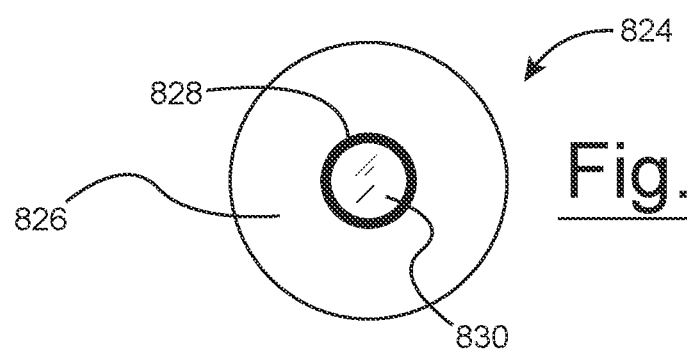
FIG. 39 illustrates a top plan view of the intraocular lens of FIG. 38.
Figure 40:
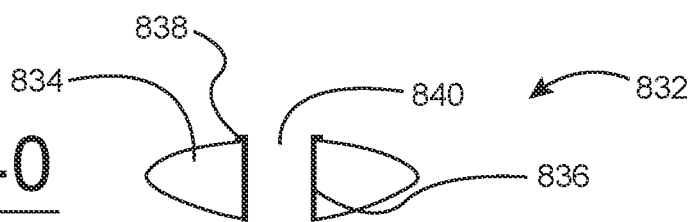
FIG. 40 illustrates a cross-sectional view of yet another embodiment of an intraocular lens with a pinhole formed by a plug member having a darkened wall.
Figure 41:
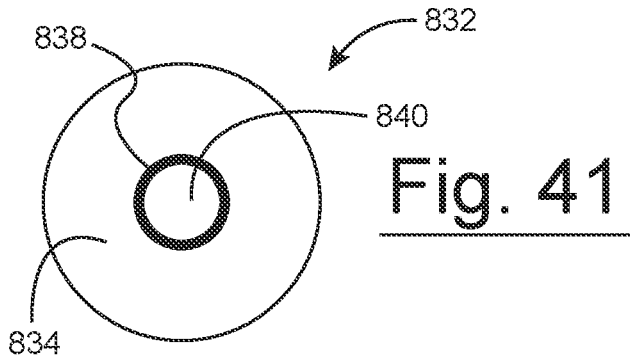
FIG. 41 illustrates a top plan view of the intraocular lens of FIG. 40.

With reference to FIGS. 38-41, two exemplary types of an intraocular lens will be described. Initially, as shown in FIGS. 38 and 39, the first type of intraocular lens 824 includes a lens body 826 with a dark mask 828 defining a virtual pinhole 830. Secondly, as shown in FIGS. 40 and 41, the second type of intraocular lens 832 includes a lens body 834 with a plug member 836 defining a pinhole 840 that passes through the lens body 834. The plug member 836 comprises a darkened wall surrounding the pinhole 840 and an outwardly protruding lip or flange 838 disposed against the anterior surface of the lens body 834.

Figure 42:
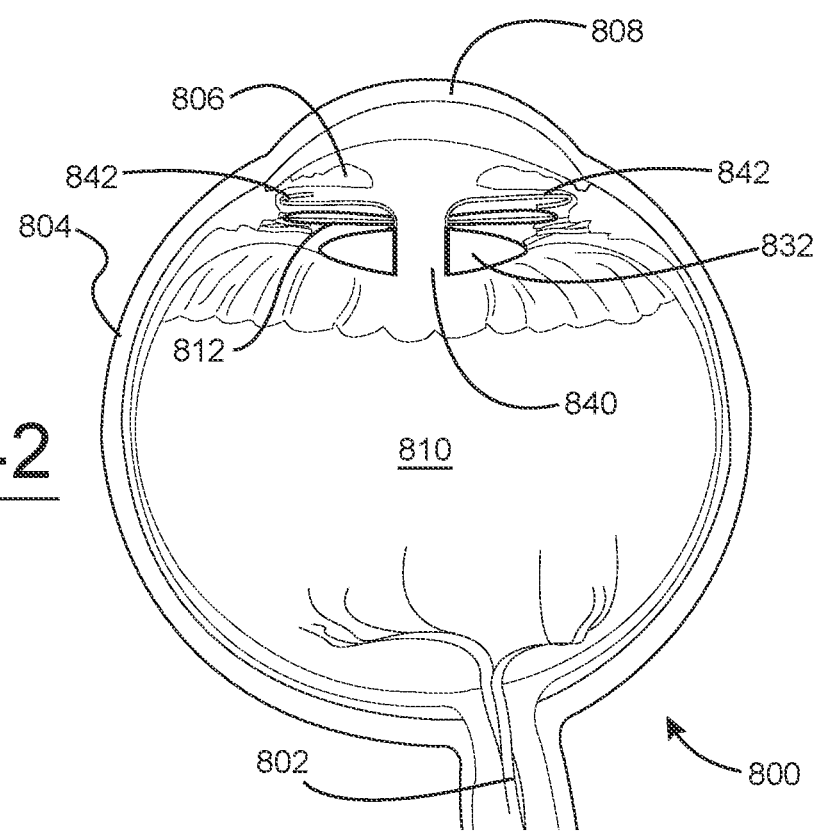
FIG. 42 is an enlarged, diagrammatic cross-sectional view of the intraocular lens shown in FIG. 40 implanted within the human eye.

Referring to FIG. 42, it can be seen that the intraocular lens 832 of FIGS. 40 and 41 is implanted behind a flattened capsular bag 812 of an eye 800. In FIG. 42, the haptics 842 extend to the anterior side of the flattened capsular bag 812 to hold the intraocular lens 832 in place.

Figure 43:
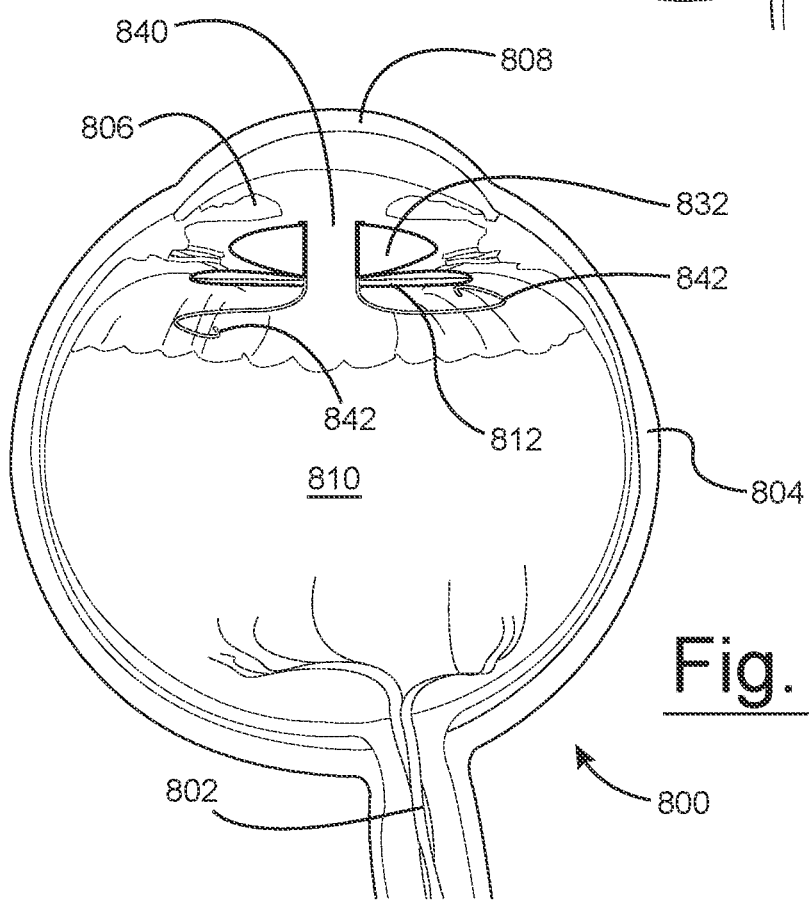
FIG. 43 is an enlarged, diagrammatic cross-sectional view of the intraocular lens shown in FIG. 40 implanted in an alternative configuration within the human eye.

Referring to FIG. 43, it can be seen that the intraocular lens 832 of FIGS. 40 and 41 is implanted in front of a flattened capsular bag 812 of an eye 800. In FIG. 43, the haptics 842 extend to the posterior side of the flattened capsular bag 812 to hold the intraocular lens 832 in place.

In one embodiment, subsequent to the initial surgery with a lens, if needed a secondary intraocular lens (IOL) with a central hole of 1-2 mm and a darkened wall can be implanted behind the iris over the initially implanted lens (i.e., primary IOL) in the postoperative period when the eye has grown to its almost normal size or normal size, where the secondary IOL is in a form of a pinhole lens with a darkened wall or a mask forming a virtual pinhole. The secondary IOL is placed in front of the first implanted lens without a pinhole to produce a pinhole effect for the primary lens, thereby permitting the child or adult to see near or far in focus through the pinhole, without the need of replacing the original implanted IOL for another IOL (see e.g., FIGS. 44 and 45). In one or more embodiments, the secondary IOL can be a collamer lens with a darkened pinhole or a virtual pinhole. In one or more embodiments, the secondary IOL can be in a form of a flat plate.

Figure 44:
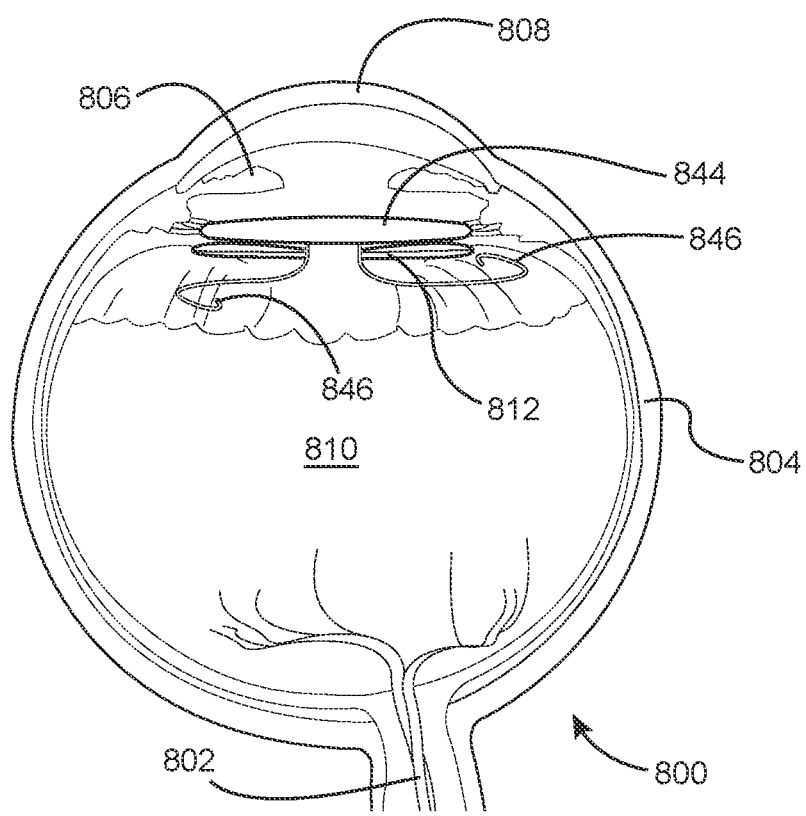
FIG. 44 is an enlarged, diagrammatic cross-sectional view of a human eye with a primary intraocular lens located overtop of the anterior and posterior capsule of the eye and the lens haptics tucked behind the anterior and posterior capsule.
Figure 45:
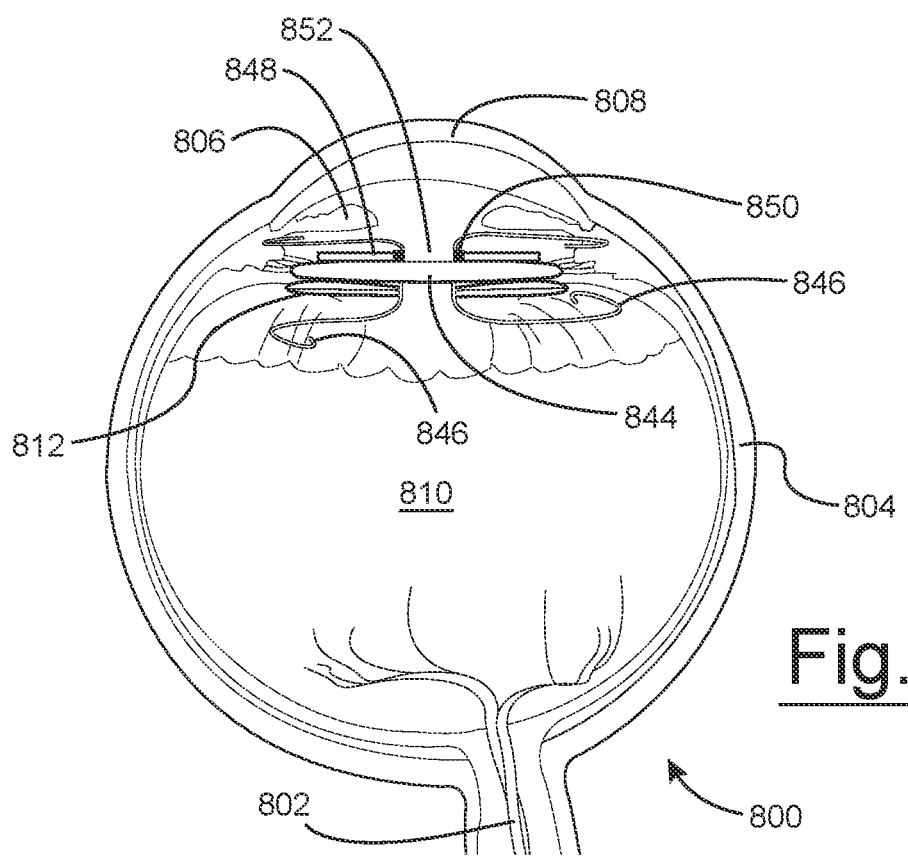
FIG. 45 is an enlarged, diagrammatic cross-sectional view of the human eye of FIG. 44 with a secondary intraocular lens provided over the primary intraocular lens, the secondary intraocular lens having a pinhole.

With reference to FIG. 44, it can be seen that a primary intraocular lens 844 is implanted in front of a flattened capsular bag 812 of an eye 800. In FIG. 44, the haptics 846 extend to the posterior side of the flattened capsular bag 812 to hold the primary intraocular lens 844 in place. It is to be understood that, in other embodiments, the primary intraocular lens 844 could also have been placed behind the flattened capsular bag 812. Then, referring to FIG. 45, it can be seen that a secondary intraocular lens 848 with a pinhole 852 surrounded by a darkened wall 850 is implanted in front of the primary intraocular lens 844. In FIG. 54, similar to the primary intraocular lens 844, the secondary intraocular lens 848 is held in place within the eye 800 by haptics. It is to be understood that, in other embodiments, the primary intraocular lens 844 could also be provided with a pinhole.

In one embodiment, in the case of a congenital or traumatic cataract, cataract extraction is done, and an IOL with a pinhole formed by a darkened wall or an IOL with a virtual pinhole formed by a mask is placed in the lens capsule after removal of the cataract with or without posterior capsulotomy. The IOL can be made of any polymeric material, such as silicone, methacrylate, or any other non-biodegradable rigid or flexible polymer, hydrogel, or collamer.

In one embodiment, the most important period for development of the retinal function is within 2 months after birth, therefore a cataract removal and replacement with an intraocular lens with a central pinhole formed by a darkened wall, or a circular mask creating a virtual pinhole, or any other conservative therapy can provide the best visual function. However, this surgery has to be weighed against increased risk for the child because of the need for a systemic anesthesia, and the complexity of surgery because of the small eye of a child.

In one embodiment, regardless of the timing of the surgery, the second important considerations affecting the result of the surgery are inflammation and glaucoma. A careful removal of the lens cortex, and creation of anterior and posterior capsulotomy and vitrectomty and intravitreal slow release medication is used to counter inflammation and glaucoma, which can reduce the postoperative complications.

In one embodiment, the two step procedure can potentially be an acceptable alternative methodology in which the pars plicata approach removes the anterior vitreous, followed with a posterior central capsulotomy, removal of the lens cortex, and the lens epithelial cells followed with a posterior vitrectomy and an anterior capsulotomy, and subsequent implantation of a pinhole lens with darkened wall or an IOL with virtual hole is implanted through a small corneal incision over the lens capsule or implanted behind both portions of the lens capsule while the haptic remains before the two leaves of the capsule. After which, two to three anti-inflammatory slow release agents are administered to the patient with or without a steroid. The subsequent postoperative procedure (i.e., the second step) for correction of the refractive power of the lens can be the addition of a refractive plate or collamer lens with a central pinhole formed by a darkened wall or a plate with a virtual hole that has a refractive power to compensate for the previously implanted IOL. The refractive plate or collamer lens is implanted through a small incision in front of the previous IOL that is located in the posterior chamber. The postoperative procedure includes the same medication and visual training for prevention of amblyopia so that the child uses both eyes seeing through both pinholes of the IOLs which keep the eyes in focus for far and near bilaterally (see e.g., FIGS. 42 and 43). If needed, prismatic correction helps keep the eye in focus.

In one embodiment, after congenital cataract extraction, glaucoma is frequently observed because of post-surgical inflammation that can negatively influence the result of the surgery.

In one embodiment, after the IOL with pinhole and darkened wall is implanted in the eye of the patient, one or more of the following medications are administered to the patient: one or more inflammatory pathway inhibitors with or without steroids, such as Rock inhibitors, Fasudil, hydrochloride, or ROCK2, Fasudill-(5-Isoquinolinesulfonyl)-2 Methylpiperazine Calcium Channel Blockers, or as SAR407899, or an inhibitor of cyclic nucleotide dependent- and Rho-kinases GSK 269962, potent and selective ROCK inhibitor GSK 429286, selective Rho-kinase (ROCK) inhibitor H1152 dihydrochloride, selective Rho-kinase (ROCK) inhibitor Glycyl H 1152 dihydrochloride, selective Rho-kinase (ROCK) inhibitor; one or more selective analogues of H1152, cell-permeable, selective Rho-kinase inhibitor OXA 06 dihydrochloride, potent ROCK inhibitor PKI1447 dihydrochloride, potent and selective ROCK inhibitor; antitumor SB 772077B, potent Rho-kinase inhibitor; vasodilator SR 3677 dihydrochloride, potent, selective Rho-kinase (ROCK) inhibitor TC-S7001, potent and highly selective ROCK inhibitor Y-27632 dihydrochloride, Botox or botulinum toxin; or a GSK inhibitor, such as synthetic small-molecule ATP-competitive inhibitors, and substrate-competitive inhibitors, non-ATP-competitive inhibitors, where FRAT/GBP competes with Axin inhibiting GSK-3 activity or anti-integrins such as Risuteganib, vedolizumab, anti-integrins, such as abciximab, Eptifibatide, Tirofiban, αIIbβ3 antagonists, Natalizumab, 3 mg to ±52 μg/mL, MLN-00002, Firategrast, IVL745, antagonists of αvβ3 and/or αvβ5 integrins, LM609, Vitaxin, Abegrin, CNTO95, Cilengitide. MLD-based disintegrins, L000845704, SB273005, Volociximab, JSM6427 in a slow release polymeric compound, such as polylactic acid, polyglycolic acid, or PLGLA; or JSM6427 or dissolved in a liquid semifluorinated alkanes or other liquids with other medications, or as polymeric slow release nanoparticles or as combinations or as liposomes, or porous silicon nanoparticles or as an implant with the size of 50-100 microns or more and a length of 1 millimeter to ten millimeters or more, etc. to release the medication slowly for 4-8 months or more.

In one embodiment the surgery may be completed as described without implantation of an IOL in the eye to avoid postoperatively induced inflammation. In such a case, the refractive correction is done with a contact lens or glasses and the IOL with a central pinhole and darkened wall or with a circular mask can be implanted with the proper refractive power in the eye behind the iris at a different stage in the sulcus, pars plana, over the remaining lens capsule with a central capsulotomy and posterior capsulotomy when the eye has grown larger, such as 3-6 years or older. The same procedure can be used after any traumatic injury in which the lens has been damaged.

In one embodiment, the postoperative anti-inflammatory agents with or without antibiotics can be applied topically or administered inside the eye or injected under the subconjunctiva to treat the eye for a long period of time.

In one embodiment, if the inflammatory response is severe, in addition to the steroids and Rock inhibitors, one administers a tissue plasminogen activator to dissolve fibrinous exudates.

In one embodiment, with the same combination therapy of the steroids and Rock inhibitors, a tissue plasminogen activator can be administered to prevent post-operative cystoid macular edema and retinal detachment by preventing scar formation or traction on the retina.

In one embodiment, the amblyopia therapy is continued with intermittent occlusion of the good eye for a desired period of time until both eyes maintain good vision along with the prismatic and glasses as needed.

Any of the features, attributes, or steps of the above described embodiments and variations can be used in combination with any of the other features, attributes, and steps of the above described embodiments and variations as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. An apparatus for implantation in an eye, the apparatus comprising:
   a lens body for providing vision correction for a patient, said lens body having a central aperture and at least one haptic extending from said lens body, and said lens body is configured as one of: a diffractive lens or a refractive lens;
   wherein said central aperture has a form of a circular hole extending fully through said lens body when said apparatus is implanted in the eye;
   wherein said central aperture includes an insert received within said central aperture, said insert having a predetermined shape before placement in said lens body and the same predetermined shape after placement in said lens body;
   wherein said lens body is formed from a substantially transparent material and said central aperture includes a darkened perimeter; and
   said darkened perimeter of said central aperture being formed by a darkened internal wall of said insert extending through said lens body from an anterior surface to a posterior surface of said lens body.

2. The apparatus of claim 1 wherein said lens body has a first index of refraction and the substantially transparent material forming said lens body is configured to have a second index of refraction when subjected to a laser.

3. The apparatus of claim 1 wherein said lens body includes a UV-absorbent peripheral portion.

4. The apparatus of claim 1 wherein said lens body further comprises:
   a first femtosecond laser modified index of refraction zone having a first index of refraction and being proximate to, and surrounding, said central aperture; and
   a second femtosecond laser modified index of refraction zone having a second index of refraction being different than said first index of refraction and being located at a peripheral portion of said lens body, inside an outer border of said lens body, for providing an expanded panoramic image to a peripheral retina of a user of said apparatus.

5. The apparatus of claim 1 in combination with an IOL and arranged such that said apparatus overlies and is anterior of said IOL when implanted in the eye.

6. The apparatus of claim 1 wherein said lens body further comprises:
   a first femtosecond laser modified index of refraction zone having a first index of refraction and covering 20% of the total surface area of said anterior surface of said lens body configured for near focus;

a second femtosecond laser modified index of refraction zone having a second index of refraction being different than said first index of refraction and covering 40% of the total surface area of said anterior surface of said lens body configured for intermediate focus; and a third femtosecond laser modified index of refraction zone having a third index of refraction being different than said first index of refraction and said second index of refraction, and said third femtosecond laser modified index of refraction zone covering 40% of the total surface area of said anterior surface of said lens body configured for far focus.

7. The apparatus of claim 1 wherein said lens body further comprises a sprayed coating of a nanoparticle composition on said anterior surface to produce a nanostructured surface.

8. The apparatus of claim 1 wherein said lens body is in a form of an intraocular lens configured to be implanted in the eye to replace a natural lens of the eye;
   wherein the at least one haptic extending from said lens body comprises a plurality of haptics configured to reach to a ciliary body of the eye so as to stabilize the intraocular lens; and
   wherein the intraocular lens is configured to correct a refractive power of the eye and extend a focal point of the eye from a far point to a near point continuously, while simultaneously correcting a refractive error of the eye.

9. The apparatus of claim 8 wherein the patient is a child with a congenital cataract or a traumatic cataract, and bilateral implantation of the intraocular lens is configured to prevent amblyopia in the child.

10. The apparatus of claim 1 wherein said lens body is in a form of a secondary intraocular lens or a collamer lens configured to be implanted in front of an existing primary intraocular lens of the eye and behind an iris of the eye;
   wherein the at least one haptic extending from said lens body comprises a plurality of haptics configured to reach to a ciliary body of the eye so as to stabilize the secondary intraocular lens or the collamer lens; and
   wherein the secondary intraocular lens or the collamer lens is configured to correct a refractive power of the eye and extend a focal point of the existing intraocular lens from a far point to a near point continuously, while simultaneously correcting a refractive error of the eye.

11. The apparatus of claim 10 wherein the patient is a child with a congenital cataract or a traumatic cataract, and bilateral implantation of the secondary intraocular lens or the collamer lens is configured to prevent amblyopia in the child.

12. The apparatus of claim 1 wherein said central aperture of said lens body is in a form of a central pinhole with a diameter between 1 millimeter and 2 millimeters.

13. The apparatus of claim 1 wherein said insert has a form selected from the group consisting of: (i) a cylindrical spring, (ii) a conical spring, (iii) a solid cylindrical plug, (iv) a solid frustoconical plug, and (v) a hollow plug.

14. A method of implanting the apparatus of claim 8 in an eye, the method comprising steps of:
   obtaining said intraocular lens of claim 8;
   forming a small incision in a limbus of the eye, or in a sclera of the eye near a pars plicata;
   performing an anterior capsulotomy on the eye;
   removing a lens cortex and a nucleus of the eye;
   performing a posterior capsulotomy on the eye;
   removing vitreous material around a region of the posterior capsulotomy performed on the eye;
   flattening a capsular bag of the eye;
   inserting said intraocular lens into the eye via the small incision; and
   implanting said intraocular lens in the eye in front of the flattened capsular bag or behind the flattened capsular bag, the plurality of haptics stabilizing said lens by reaching the ciliary body of the eye;
   whereby said intraocular lens corrects a congenital cataract or traumatic cataract of the eye and extends the focal point of the eye from the far point to the near point continuously, while simultaneously correcting the refractive error of the eye.

15. A method of implanting the apparatus of claim 8 in an eye, the method comprising steps of:
   obtaining said intraocular lens of claim 8;
   forming a small incision in a sclera of the eye near a pars plana;
   performing an anterior vitrectomy on the eye;
   performing a posterior capsulotomy on the eye;
   removing a lens cortex and a nucleus of the eye;
   performing an anterior capsulotomy on the eye from a backside of a capsular bag;
   flattening the capsular bag of the eye;
   inserting said intraocular lens into the eye via the small incision; and
   implanting said intraocular lens in the eye in front of the flattened capsular bag or behind the flattened capsular bag, the plurality of haptics stabilizing said lens by reaching the ciliary body of the eye;
   whereby said intraocular lens corrects a congenital cataract or traumatic cataract of the eye and extends the focal point of the eye from the far point to the near point continuously, while simultaneously correcting the refractive error of the eye.

16. A method of implanting the apparatus of claim 10 in an eye, the method comprising steps of:
   obtaining said secondary intraocular lens or said collamer lens of claim 10;
   forming a small incision in a limbus of the eye, or in a sclera of the eye near a pars plicata;
   performing an anterior capsulotomy on the eye;
   removing a lens cortex and a nucleus of the eye;
   performing a posterior capsulotomy on the eye;
   removing vitreous material around a region of the posterior capsulotomy performed on the eye;
   flattening a capsular bag of the eye;
   inserting said secondary intraocular lens or said collamer lens into the eye via the small incision; and
   implanting said secondary intraocular lens or said collamer lens in the eye in front of the existing primary intraocular lens of the eye and behind the iris of the eye, the plurality of haptics stabilizing said lens by reaching the ciliary body of the eye;
   whereby said secondary intraocular lens or said collamer lens corrects a congenital cataract or traumatic cataract of the eye and extends the focal point of the eye from the far point to the near point continuously, while simultaneously correcting the refractive error of the eye.

17. A method of implanting the apparatus of claim 10 in an eye, the method comprising steps of:
   obtaining said secondary intraocular lens or said collamer lens of claim 10;
   forming a small incision in a sclera of the eye near a pars plana;
   performing an anterior vitrectomy on the eye;
   performing a posterior capsulotomy on the eye;
   removing a lens cortex and a nucleus of the eye;

performing an anterior capsulotomy on the eye from a backside of a capsular bag;

flattening the capsular bag of the eye;

inserting said secondary intraocular lens or said collamer lens into the eye via the small incision; and implanting said secondary intraocular lens or said collamer lens in the eye in front of the existing primary intraocular lens of the eye and behind the iris of the eye, the plurality of haptics stabilizing said lens by reaching the ciliary body of the eye;

whereby said secondary intraocular lens or said collamer lens corrects a congenital cataract or traumatic cataract of the eye and extends the focal point of the eye from the far point to the near point continuously, while simultaneously correcting the refractive error of the eye.

* * * * *